United States Patent
Smith et al.

(10) Patent No.: US 11,275,215 B2
(45) Date of Patent: Mar. 15, 2022

(54) DIRECT LASER WRITING AND CHEMICAL ETCHING AND OPTICAL DEVICES

(71) Applicant: RENISHAW PLC, Wotton-Under-Edge (GB)

(72) Inventors: Brian John Edward Smith, Dursley (GB); Calum Ross, Edinburgh (GB); Robert Thomson, Edinburgh (GB)

(73) Assignee: Heriot Watt University, Edinburgh (GB)

( * ) Notice: Subject to any disclaimer, the term of this patent is extended or adjusted under 35 U.S.C. 154(b) by 0 days.

(21) Appl. No.: 16/472,636

(22) PCT Filed: Jan. 24, 2018

(86) PCT No.: PCT/GB2018/050195
§ 371 (c)(1),
(2) Date: Jun. 21, 2019

(87) PCT Pub. No.: WO2018/138490
PCT Pub. Date: Aug. 2, 2018

(65) Prior Publication Data
US 2019/0361174 A1    Nov. 28, 2019

(30) Foreign Application Priority Data
Jan. 27, 2017  (GB) ............................ 1701355

(51) Int. Cl.
*G02B 6/32*    (2006.01)
*A61B 1/07*    (2006.01)
(Continued)

(52) U.S. Cl.
CPC ............... *G02B 6/325* (2013.01); *A61B 1/07* (2013.01); *B23K 26/18* (2013.01);
(Continued)

(58) Field of Classification Search
CPC .................................. G02B 6/325; A61B 1/07
(Continued)

(56) References Cited

U.S. PATENT DOCUMENTS 4,119,362 A * 10/1978 Holzman ................. G02B 6/32
                                                                 385/73
4,263,033 A *  4/1981 Michalek ................. D04H 1/00
                                                                 156/62.4
(Continued)

FOREIGN PATENT DOCUMENTS

CN    101081161 A    12/2007
CN    102621823 A     8/2012
(Continued)

OTHER PUBLICATIONS

Davis et al; "Writing waveguides in glass with a femtosecond laser," Optics Letters; 1996; pp. 1729-1731; vol. 21, No. 21.
(Continued)

*Primary Examiner* — Kaveh C Kianni
(74) *Attorney, Agent, or Firm* — Oliff PLC

(57) ABSTRACT

An optical device includes a unitary substrate of optically transparent material. The unitary substrate has formed therein at least one collection lens and channel, the channel for receiving an optical fibre and arranged to align the optical fibre inserted therein such that the collection lens couples light collected by the collection lens into the optical fibre.

22 Claims, 18 Drawing Sheets

(51) Int. Cl.
  *B23K 26/18* (2006.01)
  *B29D 11/00* (2006.01)
  *G02B 6/26* (2006.01)
  *G02B 23/24* (2006.01)

(52) U.S. Cl.
  CPC .......... *B29D 11/0075* (2013.01); *G02B 6/262* (2013.01); *G02B 6/322* (2013.01); *G02B 23/2469* (2013.01)

(58) Field of Classification Search
  USPC ........................................................ 385/117
  See application file for complete search history.

(56) References Cited

U.S. PATENT DOCUMENTS

| | | | | |
|---|---|---|---|---|
| 4,324,466 A * | 4/1982 | Takayama | ............ | A61B 1/0669 396/17 |
| 4,616,899 A * | 10/1986 | Schlater | ................. | G02B 6/322 385/93 |
| 4,736,662 A * | 4/1988 | Yamamoto | ............... | G01V 8/16 250/227.22 |
| 5,175,780 A * | 12/1992 | Sano | .................... | G02B 6/3514 250/227.22 |
| 5,317,656 A * | 5/1994 | Moslehi | ................ | G01J 5/0003 385/115 |
| 5,508,489 A | 4/1996 | Benda et al. | | |
| 5,573,493 A * | 11/1996 | Sauer | ................. | A61B 1/00101 600/121 |
| 5,575,757 A * | 11/1996 | Kennedy | ............ | A61B 1/00188 348/65 |
| 5,757,997 A * | 5/1998 | Birrell | ................... | B08B 7/0028 385/60 |
| 6,332,092 B1 * | 12/2001 | Deckert | ............. | G02B 23/2469 600/476 |
| 7,349,589 B2 * | 3/2008 | Temelkuran | ......... | A61B 1/0017 385/11 |
| 7,583,876 B2 * | 9/2009 | Weisser | .................... | G02B 6/06 385/116 |
| 7,647,092 B2 | 1/2010 | Motz et al. | | |
| 7,982,957 B2 | 7/2011 | Takeuchi et al. | | |
| 9,297,749 B2 * | 3/2016 | Micheels | ............ | G01N 21/359 |
| 10,094,768 B2 | 10/2018 | Wijbrans et al. | | |
| 10,254,535 B2 * | 4/2019 | Schultheis | ......... | G02B 23/2469 |
| 10,478,049 B2 * | 11/2019 | Murayama | ............ | A61B 1/0011 |
| 2001/0000316 A1 * | 4/2001 | Kawai | ................ | G02B 6/4246 385/33 |
| 2001/0049473 A1 * | 12/2001 | Hayashi | ................. | A61B 1/043 600/317 |
| 2002/0007111 A1 * | 1/2002 | Deckert | ............. | G02B 23/2469 600/177 |
| 2002/0035330 A1 * | 3/2002 | Cline | ................... | A61B 1/0638 600/476 |
| 2002/0090180 A1 * | 7/2002 | Silverbrook | .......... | B81B 7/0067 385/92 |
| 2003/0007748 A1 * | 1/2003 | Ide | ....................... | G02B 6/4292 385/88 |
| 2003/0214571 A1 | 11/2003 | Ishikawa et al. | | |
| 2003/0215234 A1 * | 11/2003 | Mine | ................... | G02B 6/4246 398/41 |
| 2004/0042705 A1 * | 3/2004 | Uchida | .................... | G02B 6/43 385/14 |
| 2004/0178462 A1 * | 9/2004 | Sakaguchi | ............ | G02B 6/4224 257/432 |
| 2004/0240813 A1 | 12/2004 | Koyagi | | |
| 2004/0264838 A1 * | 12/2004 | Uchida | .................... | G02B 6/43 385/14 |
| 2005/0043636 A1 | 2/2005 | Gaeta et al. | | |
| 2005/0065436 A1 | 3/2005 | Ho et al. | | |
| 2005/0185900 A1 * | 8/2005 | Farr | ....................... | G02B 6/4214 385/93 |
| 2006/0013541 A1 * | 1/2006 | Plickert | ................ | G02B 6/4246 385/89 |
| 2006/0023998 A1 * | 2/2006 | Williams | ............. | G02B 6/4204 385/33 |
| 2006/0124946 A1 * | 6/2006 | Fujita | ...................... | H01L 33/62 257/98 |
| 2006/0198576 A1 * | 9/2006 | Furusawa | ................ | G02B 6/32 385/24 |
| 2006/0239605 A1 * | 10/2006 | Palen | ..................... | G02B 6/423 385/14 |
| 2007/0131856 A1 * | 6/2007 | Mogi | .................... | G02B 6/4239 250/239 |
| 2007/0221639 A1 | 9/2007 | Yoshikawa | | |
| 2007/0287920 A1 * | 12/2007 | Sawada | ................ | A61B 8/4488 600/463 |
| 2008/0239070 A1 * | 10/2008 | Westwick | .............. | H04N 9/045 348/68 |
| 2008/0260331 A1 * | 10/2008 | Takeda | ................ | G02B 6/29365 385/33 |
| 2009/0092362 A1 * | 4/2009 | Mizue | .................. | G02B 6/4292 385/92 |
| 2009/0252455 A1 | 10/2009 | Ohta et al. | | |
| 2011/0194821 A1 * | 8/2011 | Fortusini | .............. | G02B 6/3853 385/88 |
| 2011/0262083 A1 * | 10/2011 | Tamura | ................ | G02B 6/4204 385/93 |
| 2012/0045176 A1 * | 2/2012 | Hsu | ....................... | G02B 6/3885 385/74 |
| 2012/0093464 A1 * | 4/2012 | Wu | ..................... | G02B 6/3845 385/58 |
| 2012/0183256 A1 * | 7/2012 | Shao | .................... | G02B 6/4292 385/39 |
| 2012/0189252 A1 * | 7/2012 | Bhagavatula | ........ | G02B 6/4214 385/79 |
| 2012/0189254 A1 * | 7/2012 | Wang | ................... | G02B 6/4292 385/93 |
| 2013/0259431 A1 * | 10/2013 | Charbonneau-Lefort | .................... | G02B 6/4214 385/89 |
| 2014/0036271 A1 * | 2/2014 | Backman | ............ | G02B 6/3807 356/446 |
| 2014/0099058 A1 * | 4/2014 | Charbonneau-Lefort | .................... | G02B 6/4284 385/33 |
| 2015/0165556 A1 | 6/2015 | Jones et al. | | |
| 2015/0268419 A1 | 9/2015 | Van Steenberge et al. | | |
| 2015/0372757 A1 * | 12/2015 | Brosnan | ................ | G02B 6/4224 398/115 |
| 2015/0377701 A1 | 12/2015 | Pawluczyk et al. | | |
| 2016/0114427 A1 | 4/2016 | Eibl et al. | | |
| 2016/0238794 A1 * | 8/2016 | Tang | ........................ | G02B 6/32 |
| 2016/0252690 A1 * | 9/2016 | Kawamura | .......... | G02B 6/4214 398/79 |
| 2016/0279707 A1 | 9/2016 | Mattes et al. | | |
| 2016/0341903 A1 * | 11/2016 | Tang | ................... | G02B 6/4246 |
| 2017/0315299 A1 * | 11/2017 | Mathai | .................. | H01L 25/167 |
| 2017/0371114 A1 * | 12/2017 | Mentovich | ............... | G02B 6/32 |
| 2018/0259732 A1 | 9/2018 | Pontiller-Schymura | | |
| 2018/0341052 A1 * | 11/2018 | Guiset | ................ | G02B 19/0028 |

FOREIGN PATENT DOCUMENTS

| | | |
|---|---|---|
| CN | 104677830 A | 6/2015 |
| CN | 106037668 A | 10/2016 |
| CN | 106255908 A | 12/2016 |
| DE | 10 2006 004 085 A1 | 8/2007 |
| JP | S61-169804 A | 7/1986 |
| JP | H04-327391 A | 11/1992 |
| JP | H05-333232 A | 12/1993 |
| JP | 2002-287059 A | 10/2002 |
| JP | 2007-041222 A | 2/2007 |
| JP | 2008-145734 A | 6/2008 |
| JP | WO2013/061590 A1 | 4/2015 |
| KR | 10-2011-0006448 A | 1/2011 |
| WO | 03/087793 A1 | 10/2003 |
| WO | 2014/125258 A2 | 8/2014 |
| WO | 2014/125280 A2 | 8/2014 |
| WO | 2016/079496 A2 | 5/2016 |

(56) References Cited

FOREIGN PATENT DOCUMENTS

| WO | 2016/156824 A1 | 10/2016 |
|---|---|---|
| WO | 2017/009468 A1 | 1/2017 |
| WO | 2019/063999 A1 | 4/2019 |

OTHER PUBLICATIONS

Thomson et al; "Ultrafast laser inscription of a 121-waveguide fan-out for astrophotonics;" Optics Letters, 2012; pp. 2331-2333; vol. 37, No. 12.
Chen et al; "Optical waveguides in crystalline dielectric materials produced by femtosecond-laser micromachining;" Laser & Photonics Reviews; 2014; pp. 251-275; vol. 8, No. 2.
Marshall et al; "Direct laser written waveguide-Bragg gratings in bulk fused silica;" Optics Letters, 2006; pp. 2690-2691; vol. 31, No. 18.
Nolte et al; "Femtosecond waveguide writing: a new avenue to three-dimensional integrated optics;" Applied Physics A—materials Science & Processing; 2003; pp. 109-111; vol. 77, No. 1.
Hirao et al; "Writing waveguides and gratings in silica and related materials by a femtosecond laser;" Journal of Non-Crystalline Solids; 1998; pp. 91-95; vol. 239 No. 1-3.
Choudhury et al; "Towards freeform microlens arrays for near infrared astronomical instruments;" Proceedings of SPIE; 2014; vol. 9151.
Wu et al; "In-channel integration of designable microoptical devices using flat scaffold-supported femtosecond-laser microfabrication for coupling-free optofluidic cell counting;" Light: Science & Applications; 2015; pp. 1-8; vol. 4, No. 8.
Sugioka et al; "Fabrication of 3D microfluidic structures inside glass by femtosecond laser micromachining;" Applied Physics A—Materials Science & Processing; 2014; pp. 215-221; vol. 114, No. 1.
Horstmann-Jungemann et al; "Nano- and Microstructuring of SiO2 and Sapphire with Fs-laser Induced Selective Etching;" Journal of Laser Micro Nanoengineering; 2009; pp. 135-140; vol. 4, No. 2.
Bhardwaj et al; "Optically produced arrays of planar nanostructures inside fused silica;" Physical Review Letters; 2006; pp. 057404-1-057404-4; vol. 96, No. 5.
He et al; "Two-photon fluorescence excitation with a microlens fabricated on the fused silica chip by femtosecond laser miromachining;" Applied Physics Letters; 2010; pp. 041108-1-041108-3; vol. 96, No. 4.
Bellouard et al; "Scanning thermal microscopy and Raman analysis of bulk fused silica exposed to low-energy femtosecond laser pulses;" Optics Express; 2008; pp. 19520-19534; vol. 16, No. 24.
Hnatovsky et al; "Pulse duration dependence of femtosecond-laser-fabricated nanogratings in fused silica;" Applied Physics Letters; 2005; pp. 014104-1-014104-3; vol. 87, No. 1.

Shimotsuma et al; "Self-organized nanogratings in glass irradiated by ultrashort light pulses;" Physical Review Letters; 2003; pp. 247405-1-247405-4; vol. 91, No. 24.
Glezer et al; "Ultrafast-laser driven micro-explosions in transparent materials;" Applied Physics Letters; 1997; pp. 882-884; vol. 71, No. 7.
Liao et al; "Formation of in-volume nanogratings with sub-100-nm periods in glass by femtosecond laser irradiation;" Optics Letters; 2015; pp. 3623-3626; vol. 40, No. 15.
Kang et al; "The mechanism of HF/H2O chemical etching of SiO2;" Journal of Chemical Physics; 2002; pp. 275-280; vol. 116, No. 1.
Marcinkevicius et al; "Femtosecond laser-assisted three-dimensional microfabrication in silica;" Optics Letters; 2001; pp. 277-279; vol. 26, No. 5.
Hnatovsky et al; "Polarization-selective etching in femtosecond laser-assisted microfluidic channel fabrication in fused silica;" Optics Letters; 2005; pp. 1867-1869; vol. 30, No. 14.
Bellouard et al; "Fabrication of high-aspect ratio, micro-fluidic channels and tunnels using femtosecond laser pulses and chemical etching;" Optics Express; 2004; pp. 2120-2129; vol. 12, No. 10.
Agarwal et al; "Correlation of silica glass properties with the infrared spectra;" Journal of Non-Crystalline Solids; 1997; pp. 166-174; vol. 209, No. 1-2.
Taylor et al; "Applications of femtosecond laser induced self-organized planar nanocracks inside fused silica glass;" Laser & Photonics Reviews; 2008; pp. 26-46; vol. 2, No. 1-2.
Canning et al; "Anatomy of a femtosecond laser processed silica waveguide [Invited];" Optical Materials Express; 2011; pp. 998-1008; vol. 1, No. 5.
Fiorin et al; "Manufacturing of microchannels in soda-lime glass by femtosecond laser and chemical etching;" 2013 Sbmo/Ieee Mtt-S International Microwave & Optoelectronics Conference (Imoc); 2013; vol. 3.
Richter et al; "Formation of femtosecond laser-induced nanogratings at high repetition rates;" Applied Physics A—Materials Science & Processing; 2011; pp. 503-507; vol. 104, No. 2.
Drs et al.; "Laser-assisted morphing of complex three dimensional objects;" Optics Express; 2015; pp. 17355-17366; vol. 23, No. 13.
Gissibl et al; "Two-photon direct laser writing of ultracompact multi-lens objectives;" Nature Photonics; 2016; pp. 554-560; vol. 10, No. 8.
Apr. 6, 2018 Search Report issued in International Application No. PCT/GB2018/050195.
Apr. 6, 2018 Written Opinion of the International Searching Authority issued in International Application No. PCT/GB2018/050195.
Jun. 14, 2017 Search Report issued in British Patent Application No. GB1701355.8.
Nov. 1, 2018 Search Report issued in British Patent Application No. GB1807830.3.
Aug. 12, 2019 Search Report and Written Opinion issued in International Patent Application No. PCT/EP2019/062460.

* cited by examiner

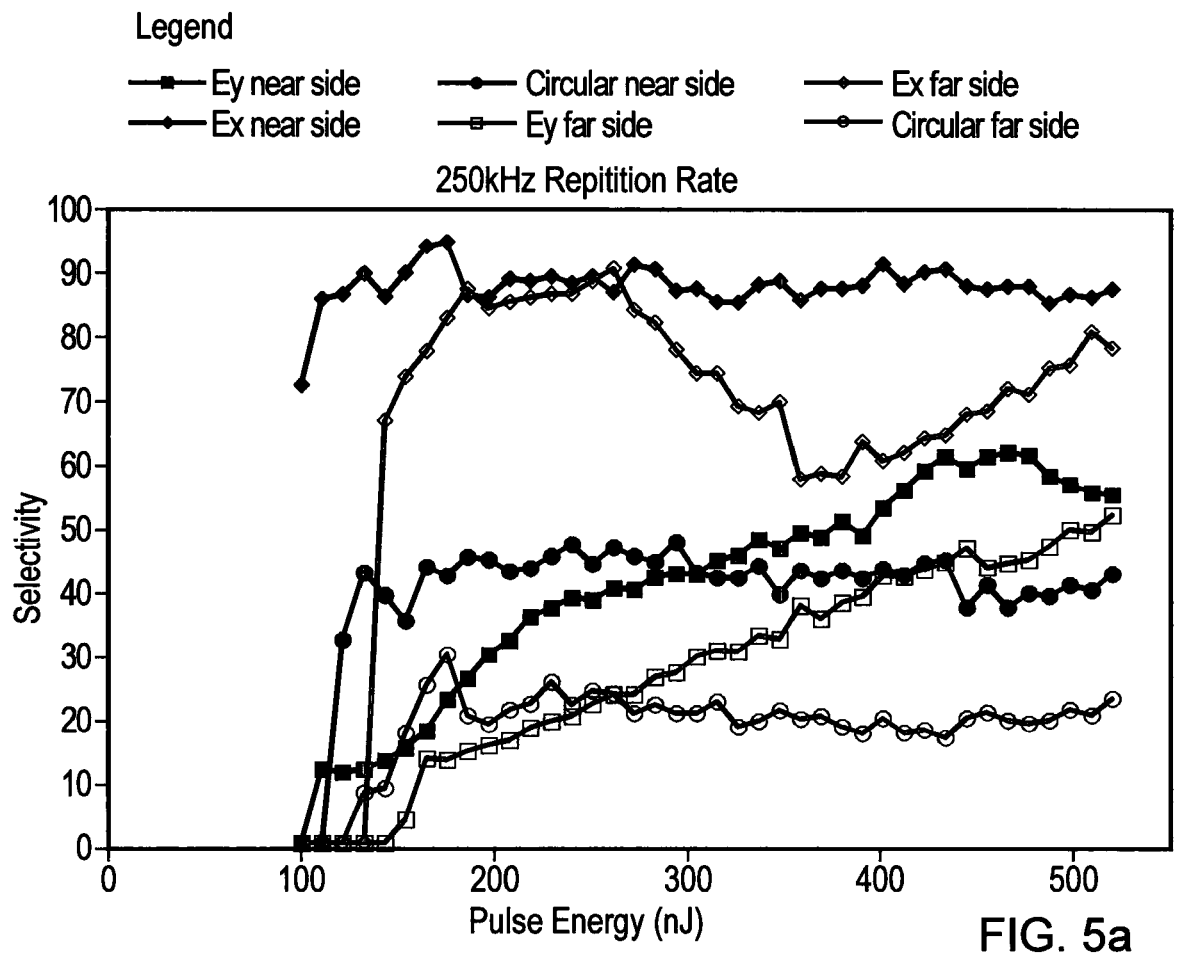
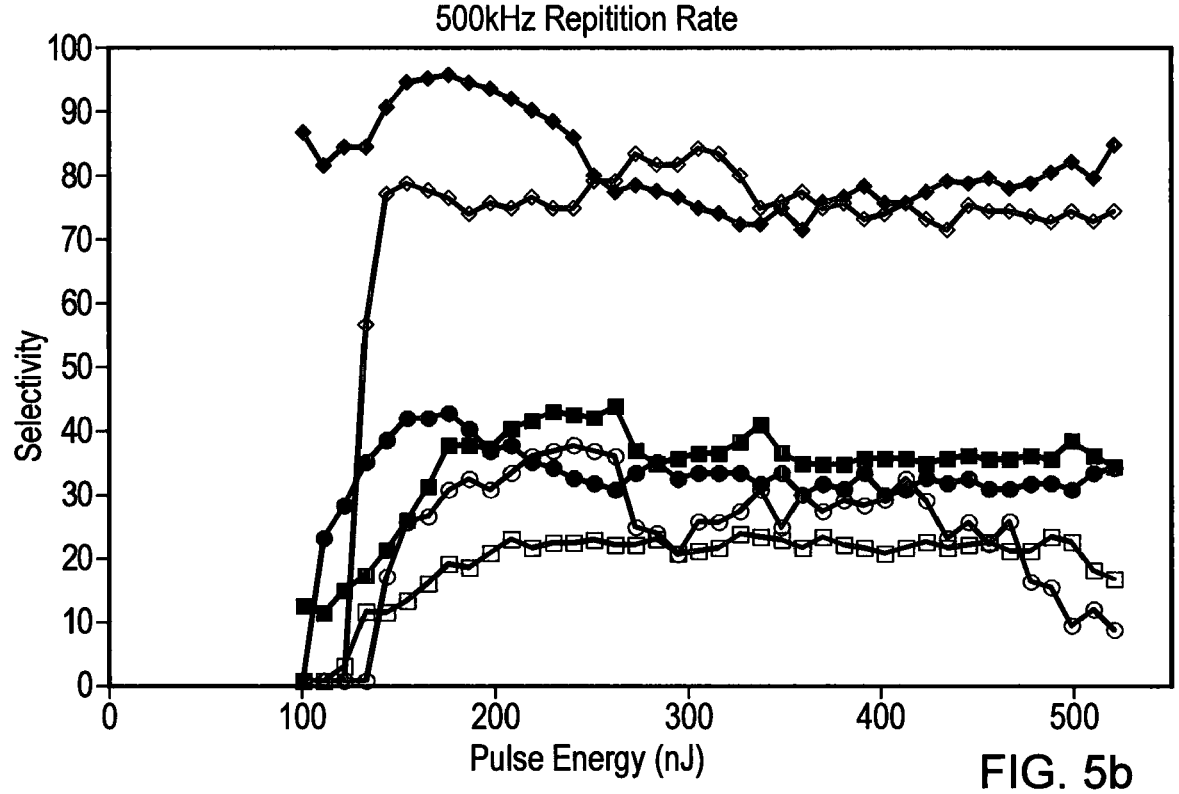

DIRECT LASER WRITING AND CHEMICAL ETCHING AND OPTICAL DEVICES

FIELD OF INVENTION

This invention concerns direct laser writing and chemical etching and optical devices. The invention has particular application to methods and apparatus for the manufacture of devices using direct laser writing and chemical etching and the devices made thereby.

BACKGROUND

It has been demonstrated that ultrafast laser pulses could be used to directly-write optical waveguides[1]. This technique, which is now known as ultrafast laser inscription (ULI), has grown to become an advanced fabrication method for complex three-dimensional (3D) waveguides[2-4]. Also known as femtosecond micromachining and direct laser writing, ULI relies on focused ultrashort pulses of sub-bandgap light to drive nonlinear multi-photon absorption within a dielectric material, resulting in a permanent change to the material's local structure. A well-known manifestation of the ULI induced modification is a change to the local refractive index, facilitating the direct inscription of 3D devices with inhomogeneous index profiles e.g. optical waveguides and volume gratings[5,6].

The modification that occurs within the focal volume is generally categorised into one of three types (Type I, II and III), depending primarily on the pulse energy and duration used during inscription. Type I describes an approximately homogeneous increase to the local refractive index resulting from a densification of $SiO_4$ tetrahedra rings that compose amorphous silica[13]. This regime is generally only accessible in fused silica using sub-200fs laser pulses[14]. Type II modification is characterised by the formation of organised 'nanogratings'; periodic alternating planes of material with high and low refractive index that form perpendicular to the electric field polarisation[15]. At higher pulse energies, Type III modification occurs where nanogratings become disordered and micro-explosions[16] create voids within the focal volume.

The formation of nanogratings has been investigated extensively in recent years but the exact underlying process remains the subject of current research. Models have been put forward based on standing wave interference[15] and nanoplasmonics[11] amongst others, and the true nature may incorporate a combination of each. The precise structuring of nanogratings suggests that a positive feedback loop exists whereby energy cumulates periodically leading to their formation. A further study demonstrated that nanogratings evolve with a shortening period due to intensity peaks that arise between adjacent nanoplanes created by the constructive interference of the scattering light from the nanoplanes[17].

A second manifestation that has gained considerable interest is that ULI can be used to increase the chemical etch-rate of the laser modified regions. The practice of using ULI in conjunction with chemical etching has gained great traction recently and enabled the fabrication of micro-optic[7], microfluidic[8] and micromechanical[9] devices on the micrometre scale with applications ranging from telecommunications to medicine.

ULI with chemical etching offers the particularly unique advantage over other glass micro-manufacturing techniques of delivering components with a freeform structure. Further, the process is adaptable, scalable and cost effective, making it well suited for the production of custom optics for a vast number of applications. However, the complex nature of ULI, stemming from the fact that many variables contribute to the overall glass modification during inscription, means that repeatable fabrication from one system to the next is not always easy.

Spectroscopic techniques are used in medical research for discriminating tissue types in the body. Many forms of spectroscopic analysis have been investigated, including that involving photon absorption, emission, and scattering. The key steps for performing spectroscopy in either of these categories is typically the same: excitation, or pump light is delivered to the target site; the light interacts with the matter and is scattered or absorbed; spectrally-changed light is collected; the collected light is dispersed to resolve the spectral information and identify atoms and molecules that constitute the matter. Often, the tissue site of interest is difficult to access and there is no direct line of sight between the tissue and probing instruments. Examples of this include the lining of the oesophagus and the distal lung.

Optical fibres have been used to perform spectroscopy in difficult to reach areas of the body. Using fibres, light is delivered and collected down the instrument channel of an endoscope passed through cavities, hollow organs or though soft tissue via a hypodermic needle. To collect as much light as possible, systems of optics are required at the distal end to guide the light onto the tissue and then back into the fibre(s). Due to the invasive nature of the operation, there is a desire to miniaturise the distal-end optical system (DOS). This miniaturisation process is challenging from a manufacturing perspective. Often intricate manual alignment of individual micro-components is required. As a result, current DOS fabrication techniques are expensive, labour intensive, and generally unsuitable for commercial manufacture.

SUMMARY OF INVENTION

According to a first aspect of the invention there is provided a method of manufacturing a device comprising laser inscribing a dielectric substrate to modify material of the substrate and chemically etching the substrate to remove the modified material at a higher etch rate than unmodified material, wherein the laser inscribing is controlled such that the modified material is of a selected type from a plurality of types of modified material having a higher etch rate than unmodified material.

By controlling the type of the modified material, a desired etch rate selectivity may be achieved, increasing the reliability of the manufacturing process.

The plurality of types of modified material may comprise or consist of Type I, Type II and Type III. The selected type may be the same for all of the modified material and preferably, is Type II. It is believed that the Type II modification achieves a greater etch-rate selectivity (the ratio between etch-rates of modified and unmodified material) compared to Type I and Type III modified material. However, for the manufacture of certain devices, it may be desirable to have differential etch-rates between different areas of modified material. Accordingly, a different selected type may be used for different areas of the substrate. Transitional regions between modified material of different types may be used to control the transport of etchant.

The plurality of types of modified material may comprise different orientations of nanogratings (periodic planes of material with high and low refractive index, for example, as achieved in Type II modified material). The selected type may be an alignment of the nanogratings substantially in an inscription direction.

The laser inscribing may be controlled to control an orientation of a polarisation of the laser beam relative to an inscription direction. The laser inscribing may be controlled such that an electric field of the laser beam is aligned substantially perpendicular to the inscription direction.

The laser inscribing may be controlled such that an energy of the laser beam is maintained above an energy threshold to achieve the selected type of modified material. The substrate may comprise silica material and the energy threshold may be between 100-200 nJ.

The laser inscribing may comprise use of a pulsed laser and the laser may be controlled to maintain a repetition rate of laser pulses within a predetermined repetition rate threshold. The substrate may comprise silica material and the repetition rate threshold may be less than 1 MHz and/or above 2 MHz.

The laser inscribing may be controlled to form layers of modified material, wherein a separation between layers of modified material is maintained within a predetermined layer separation threshold. The substrate may comprise silica material and the layer separation threshold may be between 0.7 µm and 10 µm.

The laser inscribing may be controlled by controlling the polarisation of the laser beam such that the device has a desired surface topography.

The laser inscribing may be controlled such that the polarisation of the laser beam when forming modified material at a location that will form the surface of the device is substantially perpendicular to the surface. This results in the chemical etching producing lateral ridges in the surface. Such a surface may be useful for achieving a desired optical effect, such as a diffraction grating.

The laser inscribing may be controlled such that the polarisation of the laser beam when forming modified material at a location that will form the surface of the device is oriented substantially parallel to the surface or is circularly polarised. This may result in the formation of a smoother surface than in the case of the laser beam having a polarisation that is perpendicular to the surface.

The method may comprise flame polishing the substrate after the chemical etching. Flame polishing may be used to reduce a surface roughness of the device whilst maintaining the overall surface profile.

According to a second aspect of the invention there is provided a method of generating instructions for a laser inscribing apparatus to be used in the manufacture of a device, wherein the device is to be manufactured by laser inscribing a dielectric substrate to modify material of the substrate and chemically etching the substrate to remove the modified material at a higher etch rate than unmodified material, the method comprising selecting laser inscribing parameters based upon a predetermined etch-rate selectivity achieved using the parameters and generating instructions for the laser inscribing apparatus to cause the laser inscribing apparatus to laser inscribe the substrate based upon the selected parameters.

The method may comprise determining the parameters based upon the geometry of the device to be formed. The parameters used to modify material of the substrate may depend upon an orientation of a surface of the substrate, a function of the substrate, such as a required surface roughness, and/or different etch-rates required for different volumes of modified material. The parameters may be selected to achieve these desired outcomes.

The parameters may be one or more of polarisation of the laser beam, for example relative to an inscription direction and/or surface of the device to be formed), energy of the laser beam, repetition rate of the laser beam, separation between layers of modified material, and writing speed.

According to a third aspect of the invention there is provided a data carrier having instructions stored thereon, wherein the instructions, when executed by a processor, cause the processor to carry out the method of the second aspect of the invention.

The data carrier of the above aspects of the invention may be a suitable medium for providing a machine with instructions such as non-transient data carrier, for example a floppy disk, a CD ROM, a DVD ROM/RAM (including −R/−RW and +R/+RW), an HD DVD, a Blu Ray™ disc, a memory (such as a Memory Stick™, an SD card, a compact flash card, or the like), a disc drive (such as a hard disc drive), a tape, any magneto/optical storage, or a transient data carrier, such as a signal on a wire or fibre optic or a wireless signal, for example a signals sent over a wired or wireless network (such as an Internet download, an FTP transfer, or the like).

According to a fourth aspect of the invention there is provided a method of manufacturing a device comprising laser inscribing a dielectric substrate to modify material of the substrate and chemically etching the substrate to remove the modified material at a higher etch rate than unmodified material, wherein the laser inscribing is controlled based upon instructions generated in accordance with the second aspect of the invention.

According to a fifth aspect of the invention there is provided an optical device comprising a unitary substrate of optically transparent material, the unitary substrate having formed therein at least one collection lens and channel, the channel for receiving an optical fibre and arranged to align the optical fibre inserted therein such that the collection lens couples light collected by the collection lens into the optical fibre.

The collection lens may focus the collected light to a point at an end of or within the optical fibre.

The unitary substrate may further comprise one or more transmission lenses for focussing excitation light to a focal point outside of the unitary substrate and the collection lens is arranged to couple light scattered from the focal point into the optical fibre.

The unitary substrate may have formed therein a transmission lens and a further channel for receiving a delivery optical fibre, the further channel arranged to align the delivery optical fibre inserted therein such that excitation light delivered by the delivery optic impinges on the transmission lens. The transmission lens may be a collimating lens for collimating the excitation light. The further channel may terminate closer to the transmission lens (along an optical axis of the transmission lens) than where the channel terminates relative to the collection lens (along an optical axis of the collection lens). In this way, a ratio of the area of collection lens(es) to the collimating lens can be increased compared to terminating the channel and the further channel at the same position along their respective optical axes. This ratio defines a fill factor for the unitary device, affecting a corresponding collection efficiency for the optical device.

The optical device may comprise a further, separate substrate comprising a focussing lens for focussing excitation light (which may have been collimated by the collimating lens) to a point and/or for collimating light originating from a/the point exposed to the excitation light, the further, separate substrate connected to the unitary substrate by a connecting formation. The unitary substrate may be arranged to be received by and/or receive the separate substrate. For example, the unitary substrate may comprise a male or female connecting portion to be received by or for receiving a corresponding female or male connecting portion of the separate substrate. Providing separate substrates bearing the focussing lens and the collection lens may simplify polishing, such as flame polishing, of the surfaces of each lens, whereas polishing may be more difficult if these lenses are incorporated into a single unitary substrate.

The unitary substrate may comprise a plurality of collection lenses, each collection lens having a corresponding channel associated therewith, the corresponding channel for receiving an optical fibre and arranged to align the optical fibre inserted therein such that the collection lens couples light collected by the collection lens into the optical fibre. The plurality of collection lenses may be arranged in a petal design. The petal design may be centred around the or one of the transmission lenses, such as the collimating lens.

The petal design may comprise the plurality of collection lenses providing a continuum of collection lenses in a circle or annulus. The continuum of collection lenses may be in an annulus surrounding the or one of the transmission lenses. An aperture of each collection lens may be non-circular. The aperture of each collection lens may be a circular or annulus sector. Each collection lens may extend out from the or one of the transmission lenses.

The optical device may comprise a focussing lens for collimating light originating from a/the point exposed to excitation light and directing the collimated light onto the collection lens/the plurality of collection lenses, wherein a fraction of an aperture of the collimated light filled by the collection lens/the plurality of collection lenses is greater than $2/3$, preferably greater than $7/10$ and most preferably greater than $9/10$.

The device may comprise an endoscope. The unitary device may form part of a distal end of the endoscope.

The endoscope may comprise a collection optical fibre inserted into the channel of the unitary substrate. An end of the collection optical fibre may comprise a coating to filter an excitation wavelength of excitation light from entering the collection optical fibre.

The endoscope may comprise a source for transmitting excitation light. The source may comprise a delivery optical fibre. The delivery optical fibre may be received in the further channel of the unitary substrate.

The collection optical fibre(s) and/or the delivery optical fibre may be glued in the corresponding channel or further channel.

According to a sixth aspect of the invention there is provided a method of forming an optical device according to the fifth aspect of the invention, the method comprising forming a laser inscribed substrate by selectively laser inscribing an optically transparent substrate and chemically etching the laser inscribed substrate to remove material of the substrate.

DESCRIPTION OF THE DRAWINGS

FIGS. 5a to 5d shows the results of a parameter study for planes. For each repetition rate, a graph is plotted showing the selectivity of surfaces inscribed with each polarisation state

FIG. 21 is a ray trace model of the excitation light and Raman signal generation focusing to a spot behind the DOS, wherein the rays indicate the proportion of signal collimated and collected by the lens pairs. Some light rays detected out with the DOS aperture are reflected back in towards the collection fibres but are not able to couple in;

DESCRIPTION OF EMBODIMENTS

Selective Etching

When submerged in a hydrofluoric acid (HF) solution, fused silica will dissolve to form first silicon fluoride and then hydrofluorosilicic acid following the chemical reaction[18]:

$$SiO_2 + 6HF \rightarrow H_2SiF_6 + 2H_2O.$$

The etch-rate of fused silica depends on the molecular chemistry between the glass and the etchant, as well as external factors such as the temperature. For selective etching, an aqueous solution containing between 1 and 40% acid is commonly used and etching times can vary from a few minutes to several hours. Unmodified, or pristine fused silica has an etch-rate of approximately 0.05 μm/min when submerged in a 5% HF solution. Modified Types I, II and III have each been shown to facilitate an increased etch-rate[19], and for certain inscription parameters, an increase of up to two orders of magnitude can be achieved[20]. The mechanisms that contribute to the increase in etch-rate depend on the type of modification present. For Type I modification, a decrease in the average Si—O—Si bond angle due to the shortening of the ring order sees a correlation with etch-rate[21, 22].

For Type II, etch-rate depends significantly on the orientation of the nanogratings with maximum etch-rate observed in the direction along the plane of orientation. The existence of nano-cracks[23] and porous planes of material[24] that allow faster etchant transport can potentially explain the directional etch-rate increase observed in this regime. Finally, the increased etch-rate observed for Type III modification can be explained by the presence of microvoids within the material, in addition to the modification experienced in Type I.

In order for efficient fabrication of micro-optics to be achieved, first, the form of the inscribed optic should be replicated post-etch. Expanding on this, the resolution limit of fabrication is not only set by the inscription process, but also by the etching stage. Because pristine fused silica has an intrinsic etch-rate, both modified and unmodified regions will etch when submerged in HF. The feature resolution is maximised by minimising the total time spent during the etching stage. In other words, the etching selectivity, that is the ratio between etch-rates of modified and unmodified material, should be maximised. Second, the roughness of surfaces obtained after etching should be minimised in order to maximise the optical throughput and quality of the micro-optic.

EXPERIMENTAL METHOD

Inscription Procedure

Figure 1:
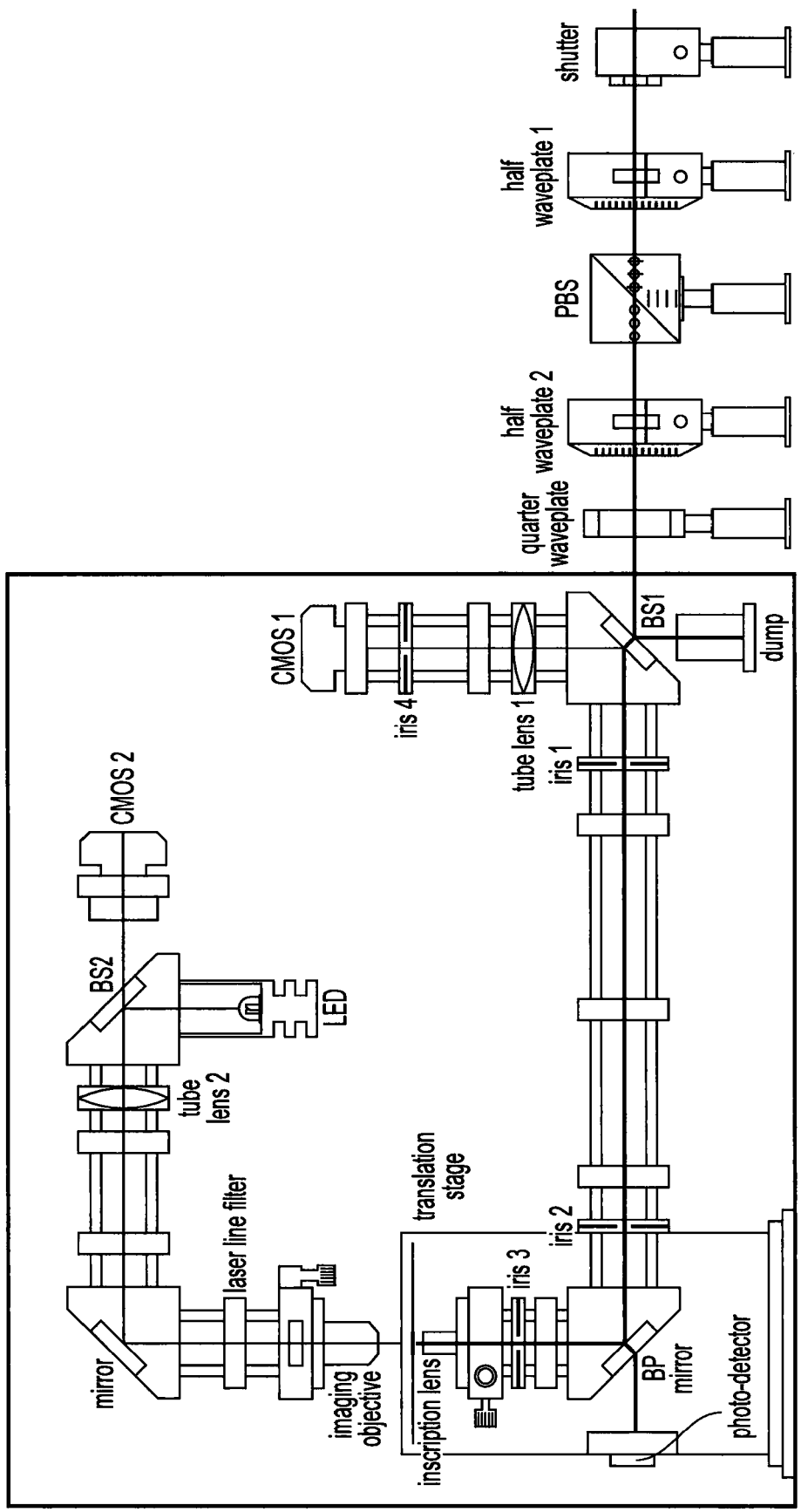
FIG. 1 is a schematic representation of apparatus for carrying out the invention.

Laser inscription was achieved using a Menlo Systems BlueCut fibre laser emitting 350 fs pulses at 1030 nm. The pulse repetition rate was selectable between 250 kHz, 500 kHz, 1 MHz and 2 MHz. Automated control of the beam's pulse energy and polarisation state was attained using a series of waveplates mounted to motorised rotational mounts and a polarising beam splitter, arranged as in FIG. 1. The beam was focused using a 0.4 NA aspherical objective to a diffraction limited spot with a theoretical $1/e^2$ spot diameter of 2.19 μm and a confocal parameter of 7.30 μm when focused in fused silica (refractive index=1.450). Samples to be inscribed, measuring 10×10×1 mm, were mounted within a square aperture, allowing interrogation from both above and below. A 3-axis ALIO Industries translation stage with 25 mm travel in each direction and 0.1 micrometre resolution was used to translate the sample through the focused beam during inscription. Smooth 3-dimensional travel was achieved using crossed roller bearings paired with a pneumatic counter balance. The stage was controlled over Ethernet via an ACS Motion Control SPiiPlus NTM Network Manager with UDMnt slave modules for each axis.

Femtosecond laser pulses are passed through a series of automated rotatable waveplates and a polarising beam splitter (PBS) in order to control their energy and polarisation. The beam is deflected, by a back polished (BP) mirror, through a 0.4 NA aspheric lens focused onto the sample from below. The power is monitored and the inscription process imaged in real-time.

Etching Procedure

All etching was performed in a 5% aqueous hydrofluoric acid (HF) solution prepared by diluting 1 part 40% stock HF to 7 parts deionised water. Samples were submerged in the etchant and placed in an ultrasonic bath for the duration of the etching time, typically between one and four hours. After etching, samples were rinsed multiple times first in deionized water and finally in an ultrasonic bath of acetone.

PARAMETER INVESTIGATION

Methodology

The process by which energy is deposited into the material during inscription can have a significant impact on the modification that occurs. Energy deposition can be controlled by varying many irradiation parameters including the wavelength, pulse duration, pulse energy, polarisation state, pulse repetition rate and focusing NA. On top of the irradiation parameters, the speed, depth and direction at which the material is translated through the spot can also affect the modification. There exists, therefore, a vast parameter space to which varying material modification can occur. Performing experiments that attempt to find global optimum parameters over the full parameter space is impractical, and there is no guarantee such optimum parameters would be conserved from one system to the next. Instead, local optimum parameters have been found, specifically with micro-optic fabrication in mind. To that end, the parameter space investigated is summarised in Table 1.

TABLE 1

| Parameter | Range | Notes |
|---|---|---|
| Laser source | Fixed | 1030 nm, ~350 fs pulse duration |
| Pulse energy | 40-520 nJ | Repetition rate dependent |
| Pulse repetition rate | 250 kHz, 500 kHz, 1 MHz, 2 MHz | — |
| Laser polarization | Parallel $\vec{E}_∥$ Perpendicular $\vec{E}_⊥$, Circular $\vec{E}_○$ | With respect to inscribed feature |
| Layer separation | 0.6-10 μm | Applies to 2D geometries |
| Inscription depth | 250, 500, 750 μm | Applies to channels |
| Translation speed | 0.5 μm/s | Fixed |

Figure 2A:
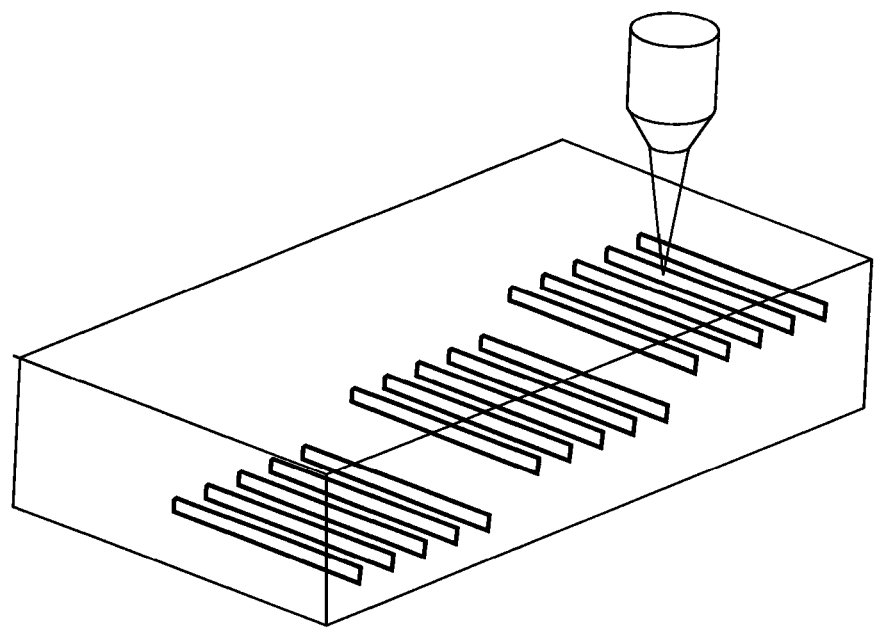
FIGS. 2a and 2b show geometries inscribed for measuring the etch-rate of (a) 1D lateral channels and (b) 2D surfaces (with inscription tool-path for each surface)
Figure 2B:
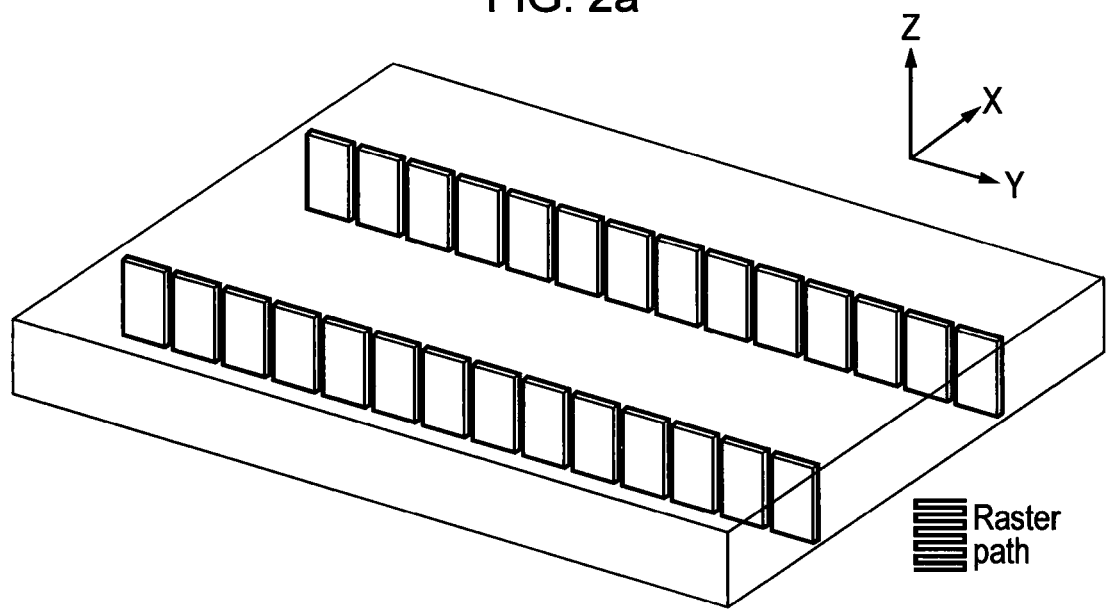

The inscription geometry also affects the etch-rate. For example, a 1D channel may etch at a different rate to a 2D surface when inscribed with identical irradiation parameters, due to the etchant transport through the material. For 3D feature fabrication, a combination of surfaces and transverse channels are commonly written. Therefore, the parameter space was investigated for each of these geometries. The forms of the structures inscribed are shown in FIGS. 2a and 2b.

Channels were inscribed by translating the substrate laterally through the laser focus along a single track once. For channels inscribed near to the edge of the glass substrate, beam clipping occurs due to the steep incident angle associated with the high NA lens. The clipping lessens the effect of modification and is more prominent at deeper inscription depths. In order to reveal the homogeneously modified material in the bulk, the edge of the glass was ground back by several tens of micrometres and polished prior to etching.

Surfaces were inscribed by raster scanning the focus through the sample, forming planes of modified material spanning the full thickness of the substrate. The surfaces were written with a width of 230 μm and a 20 μm separation between adjacent planes. The substrates were partially etched, and the etchant penetration distance through each surface measured. Selected substrates were then etched a second time to allow the etchant to penetrate fully through the sample.

Afterwards, the substrate was cleaved to reveal the modified regions and provide direct access for surface profiling and interrogation.

Results

Etching Rate Selectivity

The selectivity was measured as the ratio between the etch-rates of modified and unmodified material. Although etching of the glass is inherently three dimensional, the transport of etchant of interest to us can be simplified as unidirectional. Therefore, all etch-rates here are quoted in units of length per time. The etch-rate of virgin material was measured by submerging pristine fused silica in a 5% HF solution for 24 hours and measuring the etch-back length along the same axis as the inscribed structure in question i.e. along the long axis (y-axis) for channels and along the short side (z-axis) for surfaces. Using this method, the virgin etch-rates were measured to be 0.051±0.005 pin/minute and 0.047±0.005 μm/minute along the y- and z-axis respectively.

One-Dimensional Channels

Figure 3:
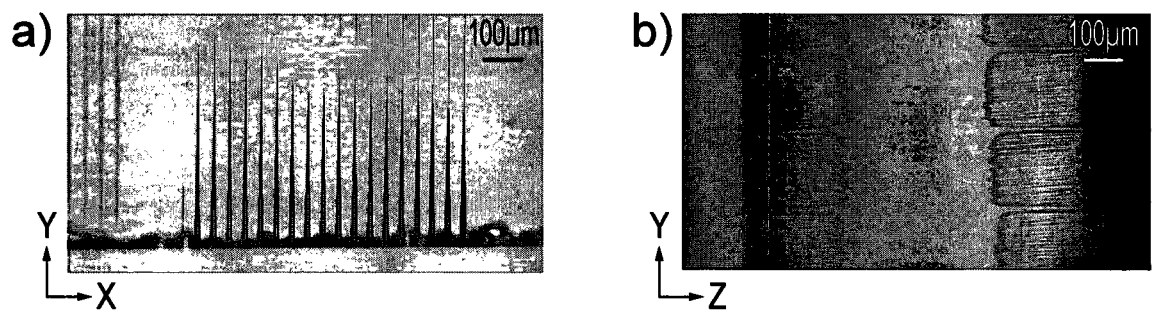
FIG. 3a is a micrograph of a group of single scan channels inscribed with increasing pulse energy from 100 to 520 nJ and etched in a 5% HF solution for 90 minutes and FIG. 3b shows etchant penetration into 2D surfaces inscribed and etched in 5% HF for 90 minutes. The etchant penetrates into both faces of the glass, denoted as near (left) and far (right) which corresponds to their distance from the inscription objective during laser writing.
Figure 4A:
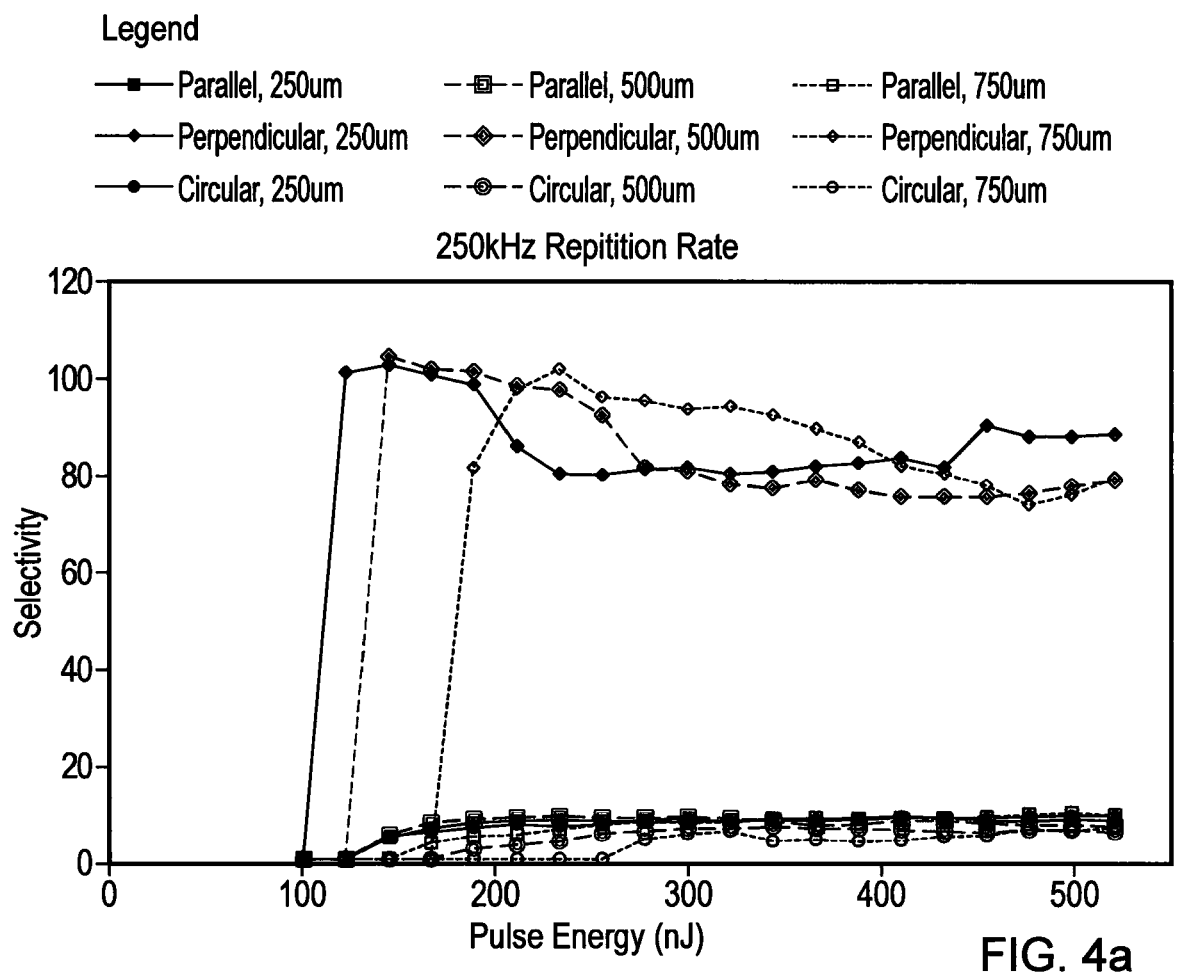
FIGS. 4a to 4d show the results of the parameter study for 1D channels. For each repetition rate, the selectivity of channels inscribed 250, 500 and 750 µm deep in the sample for each polarisation state and over the full pulse energy range was measured.
Figure 4B:
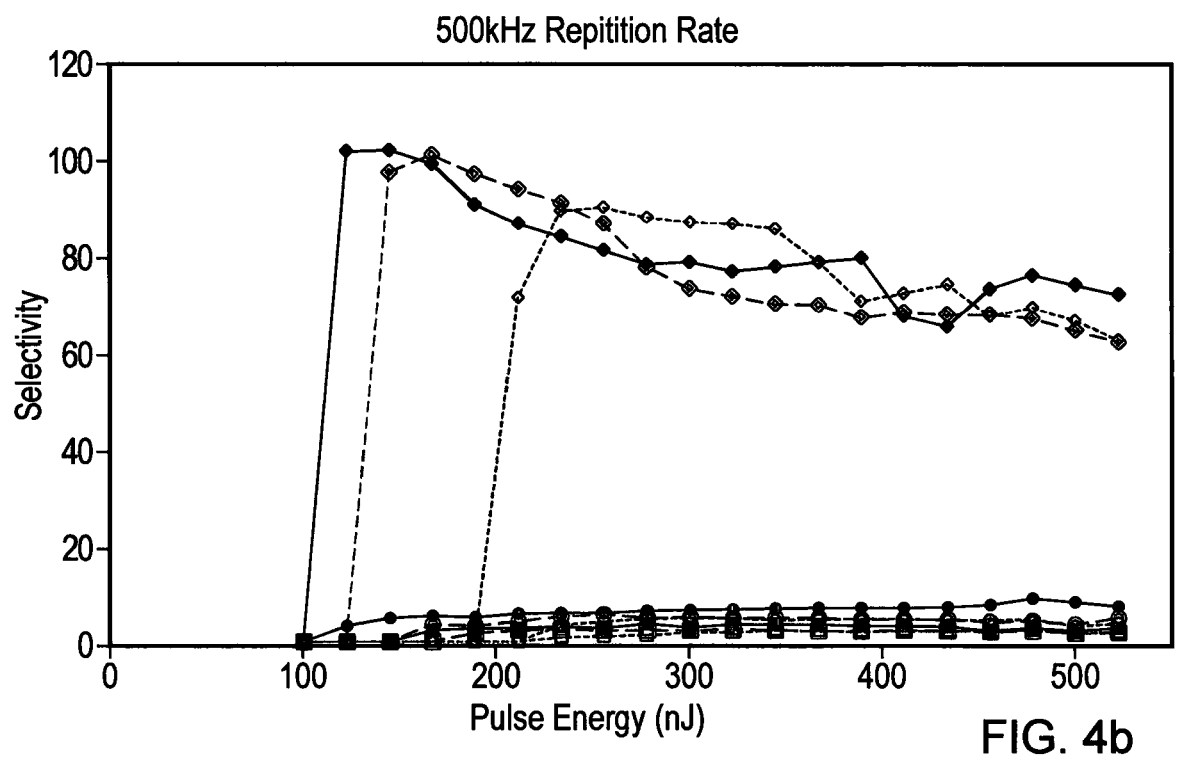
Figure 4C:
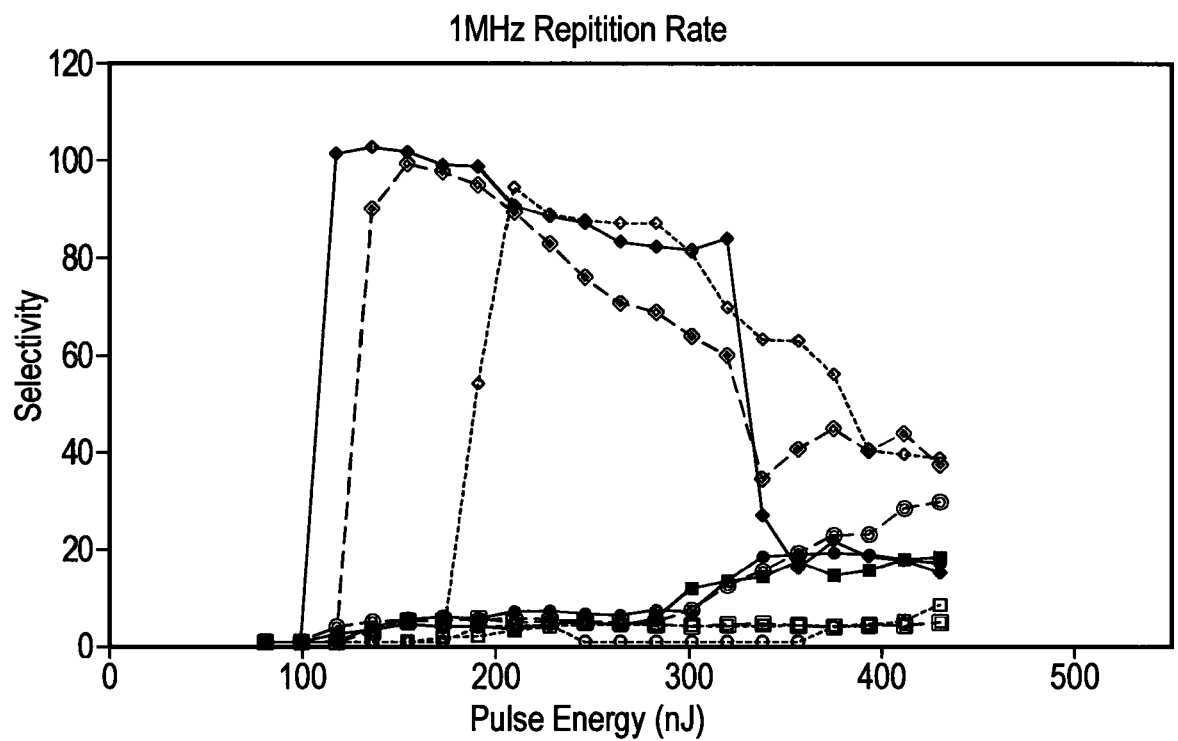
Figure 4D:
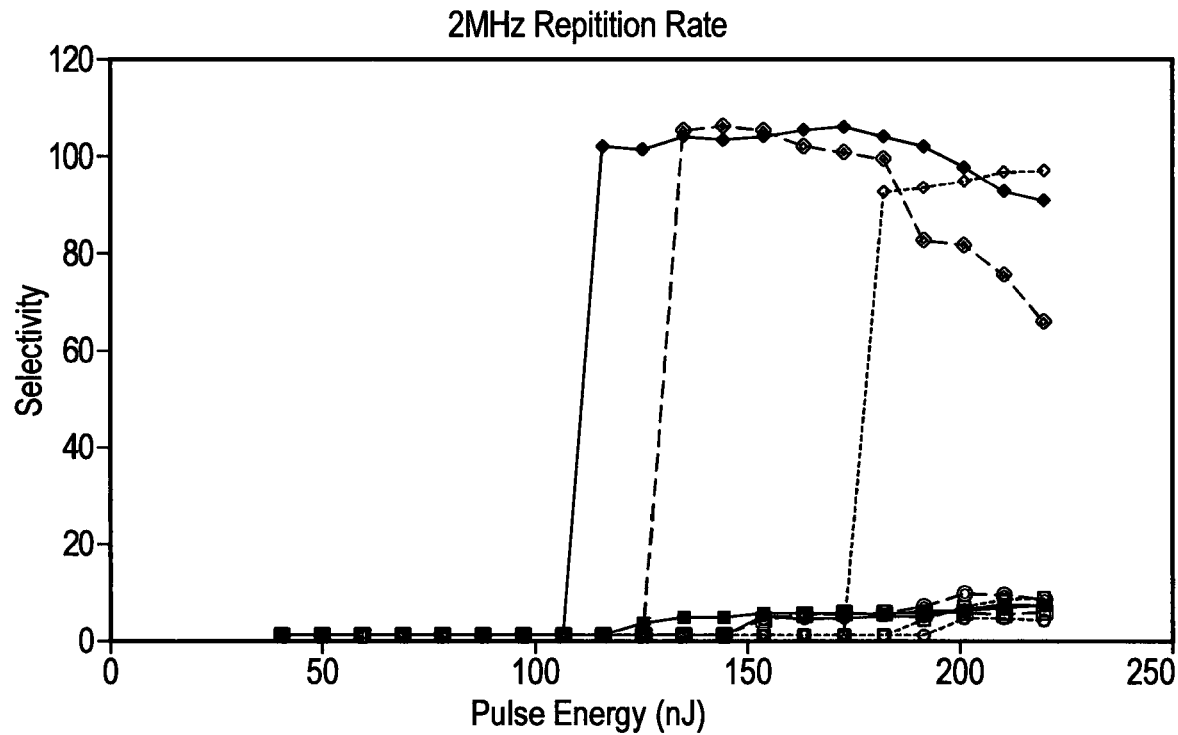
Figure 5C:
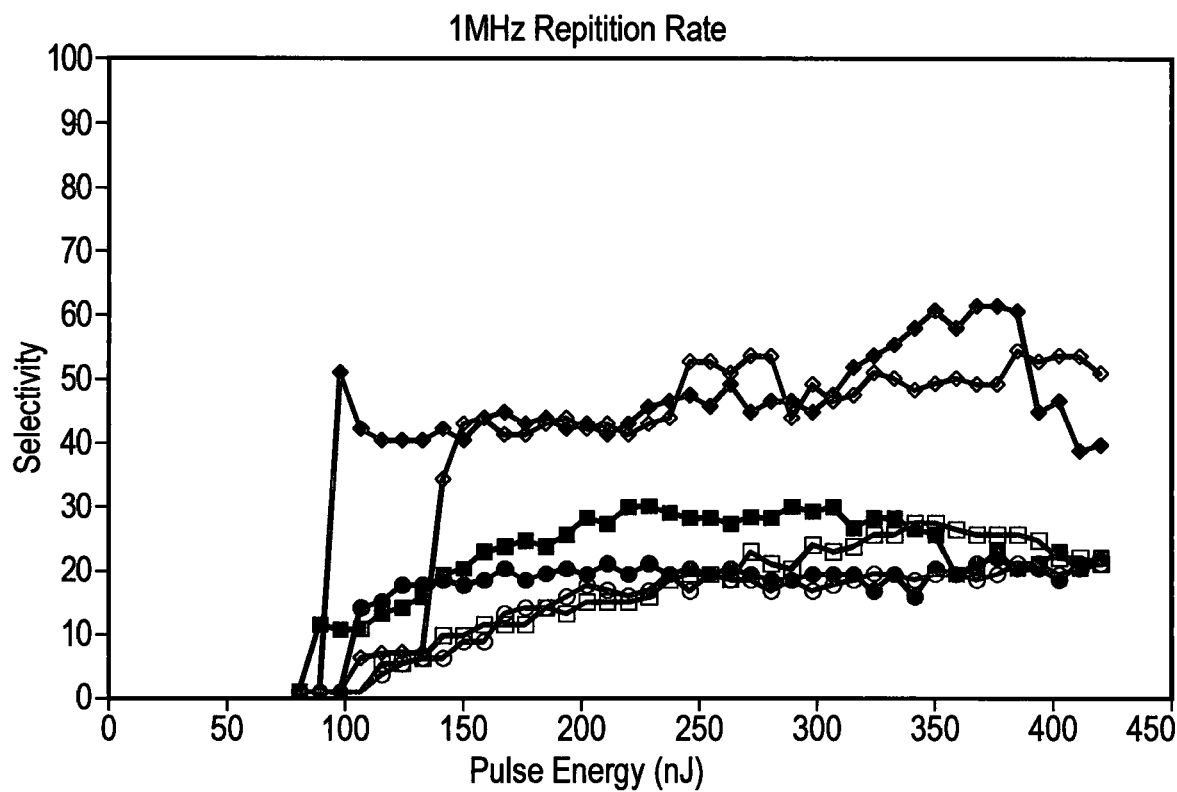
Figure 5D:
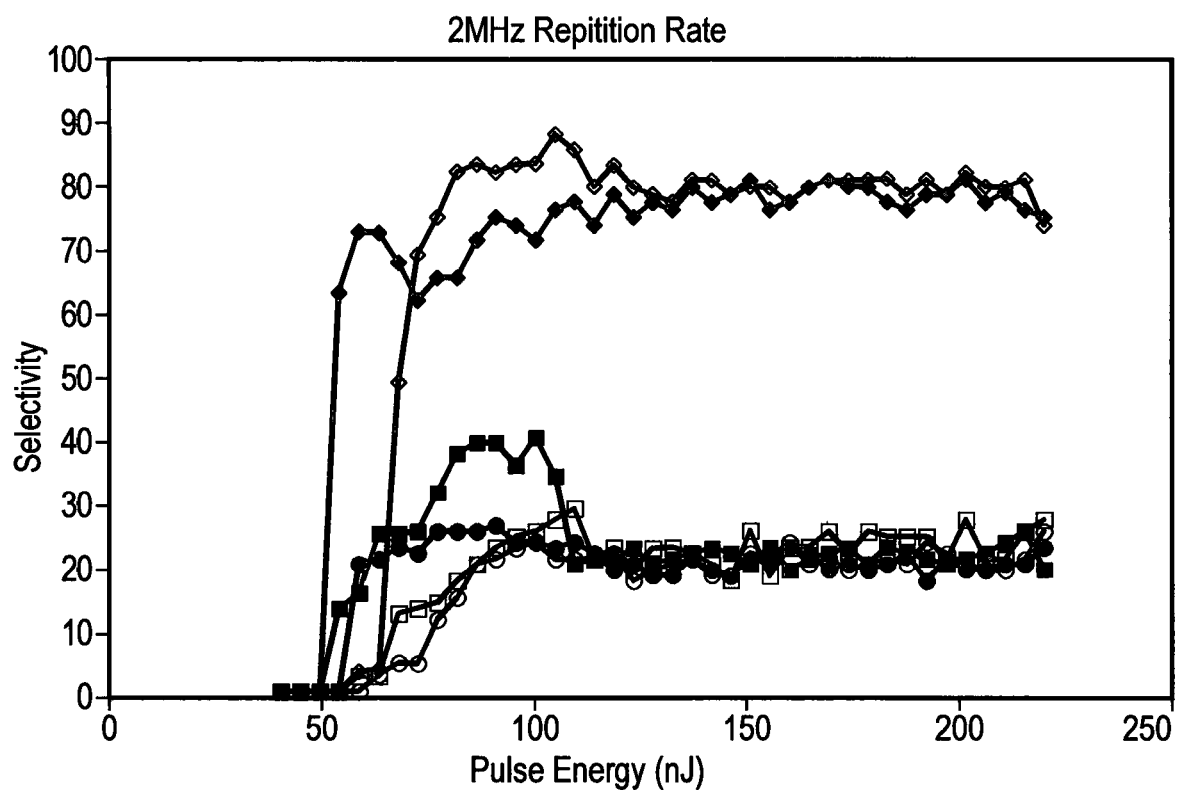

A typical micrograph of inscribed channels taken after etching is presented in FIG. 3a. The tapering of the channel, itself an indication of the selectivity, is caused by the outward etching of pristine material experienced by the channel as the etchant propagates through.

The lengths of the channels were measured and used to calculate the individual parameter set selectivities. The selectivity, S, was calculated as $$S = \frac{l}{T\varepsilon} + 1,$$

where l is the channel length, ε is the virgin material etch-rate and T is the etching time. The etch-rate as a function of pulse energy for each repetition rate and writing depth is presented graphically in FIGS. 4a to 4d.

Individual irradiation parameters are responsible for trends that were observed in the etch-rate of channels. The contribution from each parameter is summarised here:

Pulse energy: A minimum pulse energy was required, the modification threshold, before which no increase to the selectivity occurred. The sharp rise in etch-rate corresponds to modification entering the Type II regime. The modification threshold increased when inscribing deeper in the substrate. This is due to aberration of the spot focused through the glass. Modification threshold was found to be in the region of 100-200 nJ. After threshold was achieved, the selectivity continued to increase marginally for parallel and circular polarisation and decreased steadily for perpendicular polarisation. The decrease in selectivity for higher pulse energies can be explained by the expected disordering of nanogratings as the modification transitions from Type II to Type III.

Polarisation: The most significant variable in determining the selectivity was the orientation of the laser electric field. When aligned perpendicular to the inscription direction, the maximum selectivity was found to be upwards of 100 for each repetition rate compared with 5 to 10 parallel and circular polarisation. The results are in agreement with current theories that permeable nanogratings allow for fast etchant transport[25], and form perpendicular to the polarisation direction.

Repetition rate: The pulse repetition rate had a less significant influence on the etch-rate of the modified material. A sharp decrease in selectivity is found for high pulse energies at 1 MHz. This was likely due to thermal accumulation associated with the high repetition rate during inscription perhaps leading to a collapse of nanogratings.

Planes

Figure 6:
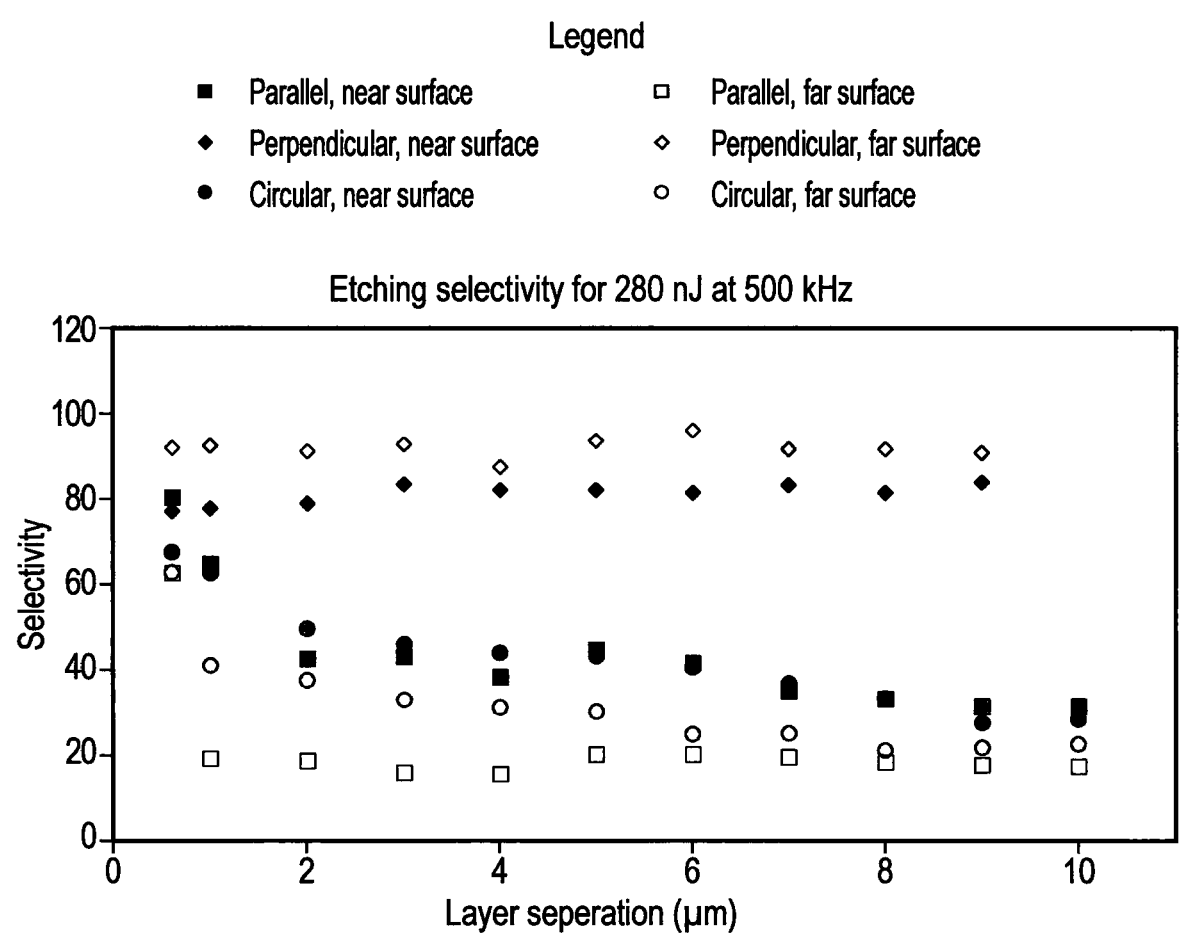
FIG. 6 is a graph showing the etch-rate as a function of the spacing between inscribed layers for each polarisation state.

After etching for ninety-minutes, the irradiated surfaces were photographed through the edge of the substrate and the etchant penetration depth measured. A typical etched surface is presented in FIG. 3b. The etch-rate selectivities, again as a function of pulse energy and for each of the parameters investigated, are plotted in FIGS. 5a to 5d. The layer separation, that is the spacing between adjacent rungs of the surface raster pattern, was additionally investigated for planes inscribed with a pulse repetition rate of 250 kHz and the results are plotted in FIG. 6.

Again, the contribution to the etch-rate from each parameter group was analysed:

Pulse energy: For surfaces, the etch-rate modification threshold was reached at approximately 100 nJ per pulse. At higher pulse energies the selectivity appeared to level off with the exception of parallel polarisation which increased gradually.

Polarisation: As with the inscribed channels, surfaces exhibit a maximum selectivity when inscribed with the incident electric field aligned perpendicular to the inscription direction. Again this is due to the alignment of nano-gratings that form within the modified material, perpendicular to the linear polarisation orientation. The result highlights the significance of polarisation in etchant transport through the modified region; when the nano-planes align along the surface, the etchant can permeate across the surface whereas, in the case of perpendicular nano-planes, the etchant can only permeate longitudinally through the substrate.

Repetition rate: Since the translation speed was kept constant throughout, the total energy deposited per unit length varies linearly with the pulse repetition rate. The repetition rate appeared to influence the selectivity only subtly, with the exception of inscription at 1 MHz which saw the average selectivity decrease by half with respect to inscription at other repetition rates. It is believed the thermal accumulation in the bulk may be responsible for the breakdown of nanogratings and the apparent decrease in etch-rate. However, the etch-rate is restored at 2 MHz where thermal accumulation is expected to be greater. Etchant transport is hindered most when transitioning between Type II and Type III modification where nanogratings begin to disorder.

Layer separation: For perpendicular polarisation, the separation between layers is observed to have little effect on the etch-rate as is represented by the flat blue curve in FIG. 6. For parallel and circular polarisation, however, the etch-rate increases as the layers get closer together. There exists a trade-off between the etch-rate and layer separation in practice because the fabrication time scales with the inverse of the layer separation. A layer separation of between 0.7 and 1 μm, appears optimal and at this level, the selectivity for circular and parallel approaches that of perpendicular polarisation.

The "inscription direction" is the direction of lateral displacement from one geometry co-ordinate to the next. For example, using the coordinate system shown in FIG. 2, the one-dimensional channels were inscribed with the inscription direction along the y-axis, by translating the sample along y. The nanogratings form perpendicular to the electric field orientation (linear polarisation angle) in the x-y plane. If a channel is inscribed along y, and the polarisation is also oriented along y in the x-y plane, then the polarisation is labelled 'parallel'. If a channel is inscribed along y, but the polarisation is oriented along x in the x-y plane, then the polarisation is labelled 'perpendicular'.

Surface Profile

Figure 7:
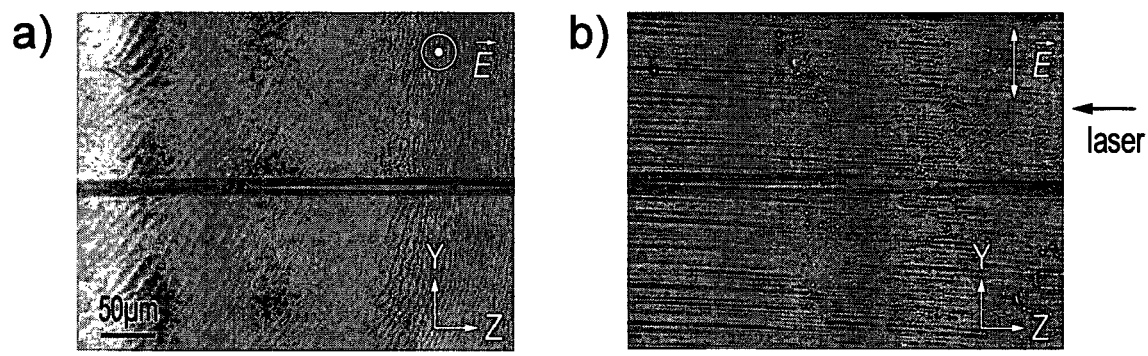
FIGS. 7a and 7b is a comparison between surfaces inscribed with the electric field aligned perpendicular to the surface (FIG. 7a) and parallel (FIG. 7b). The horizontal break indicates the spacing between one parameter and the next.

The specific modification made to each surface during inscription not only determines the etch-rate but also the surface structure obtained after etching. Imprints of the energy deposition are carried through as permanent artefacts on the surface topography. The micrographs in FIGS. 7a and 7b show significantly different forms for surfaces inscribed with the laser polarisation aligned perpendicular and parallel to the writing direction in (a) and (b) respectively.

To inspect the surfaces more closely, atomic force microscope (AFM) scans were performed over 50 by 50 μm areas. Surface topography was measured for surfaces inscribed with the polarisation linear (perpendicular and parallel to the writing direction) and circular with all other parameters kept constant. The surface topography obtained from the AFM scans are presented in FIGS. 8a to 8f.

Figure 8:
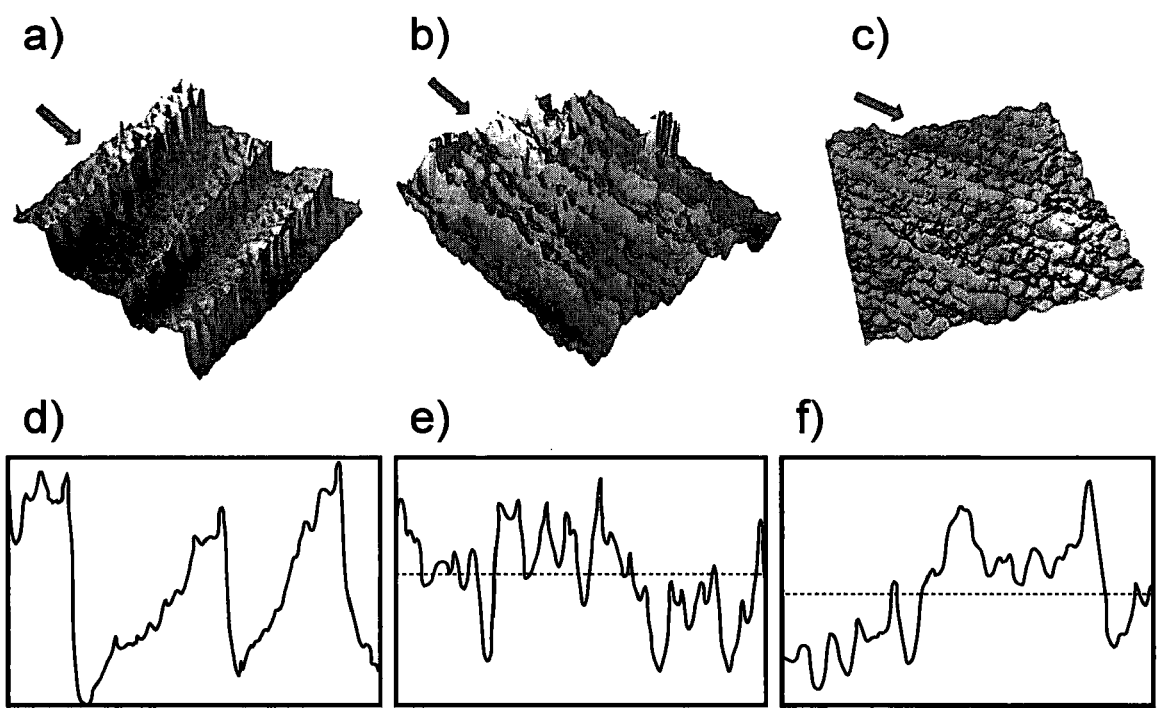
FIGS. 8a-8c show surface topography, measured with an AFM, for features inscribed with the polarisation perpendicular, parallel and circular (a to c respectively) with respect to the laser translation direction
FIGS. 8e-8f are accompanying line profiles for each surface; each line cut-out spans 50 µm and the depth of field is ~400 nm in each case.

When the polarisation state is linear and orientated perpendicular to the inscribed surface as in FIG. 8a, it is observed that lateral ridges form along the surface, approximately perpendicular to the polarisation direction. The ridges measured had a varying separation of the order of 20 μm and a step height of ~200 nm. The standard root mean squared (RMS) and peak to peak surface roughness were sampled on the planes between the ridges over 100 μm$^2$ areas and the average found to be 16.52 nm and 71.1 nm respectively.

With the polarisation aligned along the inscription direction as in FIG. 8b, the spatial separation of the surface ridges decreased by approximately one order of magnitude and rotated by 90 degrees forming longitudinally through the surface. The average sampled RMS and peak to peak surface roughness was found to be 98.8 nm and 377.9 nm respectively.

A similar surface structure was found when the incident light was circularly polarised as shown in FIG. 8c. Again the RMS and peak to peak surface roughness were measured and respective values of 85.48 nm and 357.2 nm were obtained.

Figure 9:
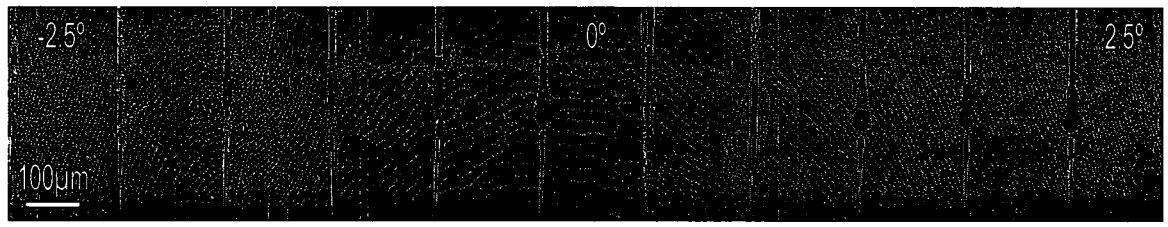
FIG. 9 is a high-contrast micrograph of surfaces inscribed with a varying laser polarisation (shown here from −2.5° to 2.5°) and etched in HF. The polarisation is perpendicular to the surface in the centre and rotates by ±0.5° for each adjacent surface.

In order to attempt to explain the origin of the periodic ridges observed in FIG. 8a, surfaces were inscribed with the linear polarisation of the inscription beam iterated in 0.5° steps through ±~7° from perpendicular to the translation direction. The etched surfaces were imaged with a standard white light reflectance microscope. The images were enhanced for clarity and stitched together, the result is presented in FIG. 9.

It is observed that as the polarisation aligned perpendicular to the surfaces, the ridge separation distance peaked. The ridge orientation also follows a well-defined pattern. When the polarisation was aligned perpendicularly, the ridges appeared horizontal. After rotating the polarisation by just 6°, the ridge angle was measured to be 87.6° to horizontal.

These observations can be explained with a model. When the nano-gratings form perpendicular to the surface (parallel polarisation), they imprint their edges directly onto the surface, with a period, s, equal to that of the nano-grating spacing, d. As the nano-gratings rotate, their period increases with one over the sine of the angle, θ, that the nanogratings make to the surface becoming infinity when θ=0. From FIG. 10b, it can be expected that $$S = \left| \frac{d}{\sin(\theta)} \right|.$$

Figure 10:
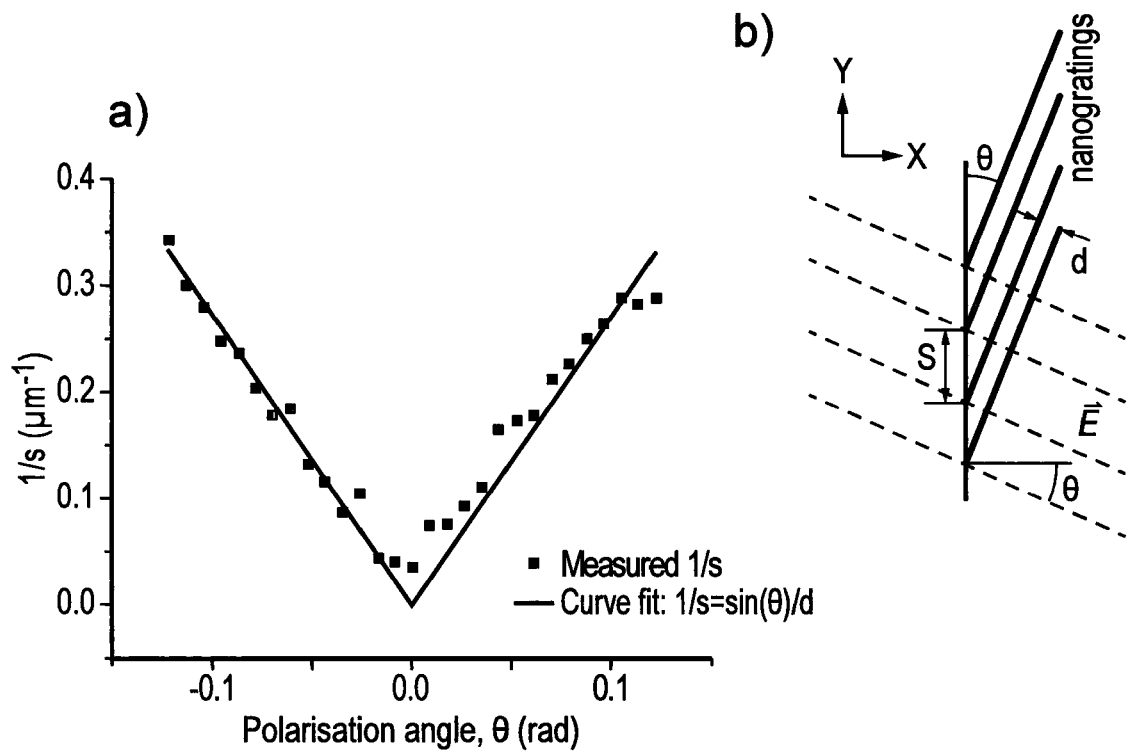
FIGS. 10a and 10b is a plot of the measured ridge separation, s, as a function of the polarisation angle, θ. A line fit was applied to the measured values allowing nanograting spacing, d, to be obtained.

To test the model's validity, a plot of θ against 1/s (inverted as to avoid the asymptote) was made, the results of which are presented in FIG. 10a. A data fit was performed suggesting good agreement between the experimental data and the values expected from the model. From the fitted curve, the nano-grating period was found to be 366±8 nm which is in line with $\lambda/2n$ (355 nm) as predicted by the nanoplasmonic model for first stage of nanograting formation[26]. A decrease in the nano-grating period near to the surface closest to the laser during inscription is observed. The nanoplasmonic model further predicts the evolution of nanogratings; as the number of pulses or total energy deposited increases, the nanograting spacing decreases. The observations can be explained by this; near to the surface the focal volume is not aberrated and so maximum modification occurs. Whereas deep in the sample the aberrated pulses contribute less to the total modification.

Discussion

It has been shown that the longitudinal selectivity of 2D surfaces is significantly increased, by a factor of 100, for polarisation aligned perpendicular to the writing direction, irrespective of the layer separation for the range investigated. The minimum pulse energy required for modification was consistently between 100 and 150 nJ with peak modification occurring around 200 nJ. Modification within this range is firmly placed in the Type II regime where the formation of nanogratings is expected. The nanograting 'footprint' on surfaces obtained after etching has been observed, and that the lateral stacking of nanoplanes forms ripples along an etched surface that contribute to the roughness of surfaces obtained. The RMS surface roughness measured in the spacing between adjacent ridges was 16.52 nm, corresponding to a five-fold reduction compared to surfaces inscribed with circularly polarised light and approximately $\lambda/50$ for 800 nm light commonly used in spectroscopic applications. It has been further observed that the spacing between ridges decreased when inscribed deeper in the substrate and attributed this to a lower effective pulse energy. To this end, precise control of the inscription beam's polarisation and pulse energy will enable alignment of the nanogratings and the surface which in principle, should see the ridge separation go towards infinity. When implemented, repeatable fabrication of structures with optical surface quality is achievable.

A summary of the optimum local parameters found for ULI micromachining is given in Table 2.

TABLE 2

| Parameter | Optical quality feature | Structual feature |
| --- | --- | --- |
| Pulse energy | 200 nJ | 260 nJ |
| Pulse repetition rate | 500 kHz | 500 kHz |
| Laser polarization | Perpendicular to surface | Perpendicular to surface |
| Layer separation | 1 μm | 6 μm |
| Translation speed | 0.5 μm/s | 1 μm/s |

Optimised Fabrication

Method

Inscription Process

To inscribe 2D structures such as lenses, the surface profile is first generated using numerical modelling or CAD software. The surface is then sliced into layers that represent single scan tool paths for the inscription laser. Starting with the layer furthest away from the inscription objective, the layers are inscribed sequentially until the full profile is obtained. This method ensures that no crossover between the modified regions and beam occurs during inscription, which may otherwise lead to unnecessary aberration. Etching channels and planes are written in addition to the lens surface in order to allow the etchant to penetrate through the substrate quickly. A typical inscription time for a lens surface was approximately twenty minutes and etching was complete after three hours.

Figure 11:
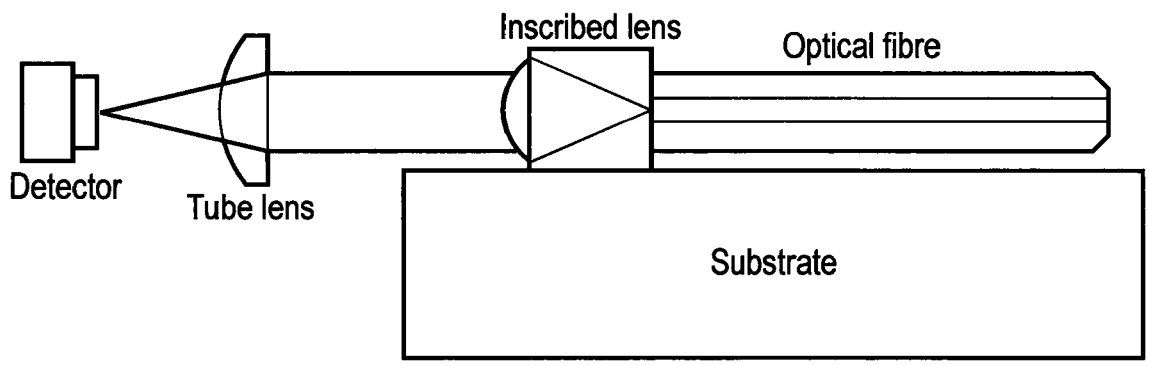
FIG. 11 is an experimental setup for microlens characterisation. Lenses are inscribed and etched onto the edge of a fused silica substrate. Light is delivered by a single mode step-index fibre and the aperture imaged by a CCD.

To characterise the quality of the fabricated lens, the surface profile, roughness and optical throughput were measured. The experimental setup for characterization is shown in FIG. 11. The lens was designed to collimate the output from a 0.13 NA, 780 HP optical fibre with a mode field diameter of 5.0 The lens was inscribed on the edge of a glass segment with a length equal to the lens' focal length as shown in FIG. 11. The fibre was brought into contact with the back edge of the lens segment and index matching fluid was used to reduce any scatter at this interface. A standard moulded aspheric was used to focus the collimated light onto a photodetector. The microlens throughput was measured by comparing the light detected emerging directly out of the fibre into free space with that transmitted through the microlens.

Flame Polishing

Flame polishing describes the process of applying heat to the surface of a material in order to reduce its surface roughness. When the material is heated, the high spatial frequency artefacts on the surface that constitute roughness heat up more quickly that the bulk substrate. There exists, therefore, a moment during heating where a fine layer on the surface becomes liquid and free to flow. Before cooling, natural surface tension attracts the liquid layer towards the bulk, tending to minimise the surface area. As a result, the high-frequency surface roughness is permanently smoothed out over the surface. Previously it has been shown that $CO_2$ laser heating can be used to morph ULI fabricated cubes into near perfect spheres with sub-nanometre surface roughness[27]. Additionally, the surface roughness of ULI fabricated surfaces has been improved by applying an oxyhydrogen flame directly[12]. A similar method is used in order to improve the surface quality of a microlens while maintaining the overall surface profile by applying heat from a precision flame directly.

Flame polishing was achieved using an oxyhydrogen flame generator with a potassium hydroxide electrolyte, providing a peak flame temperature of approximately 1800° C. The lens was brought into direct contact with the flame for a single five-second burst, after which noticeable surface polishing had occurred.

Results and Characterisation

Roughness

Figure 12:
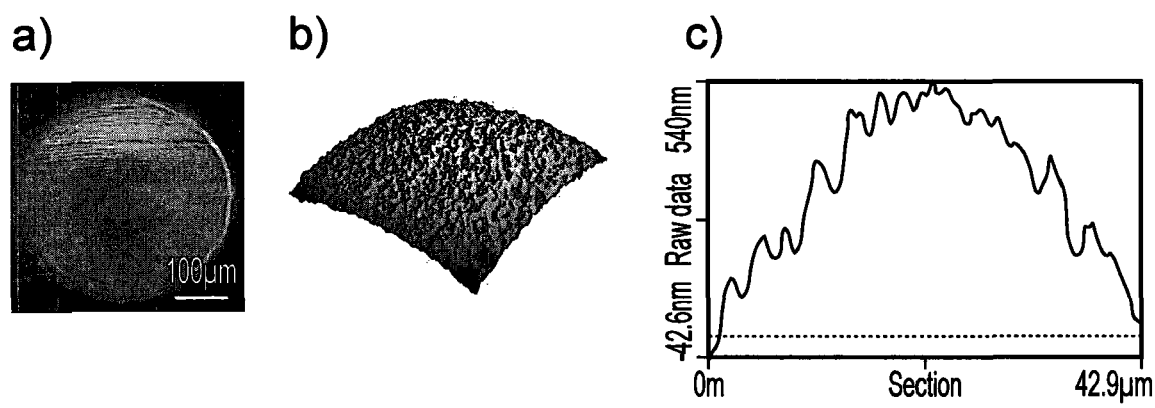
FIG. 12a is a micrograph of an inscribed and etched aspheric microlens with 400 µm diameter and 32 µm thickness and FIGS. 12b and 12c are the 3D and 2D surface profile measured with an atomic force microscope across a 42.9 µm section of the lens surface. The measured section spans 0.58 µm in height. The high spatial frequency surface, signature of HF etching, is clearly visible and quantifies an RMS surface roughness of 91.5 nm.

A microlens with 400 μm diameter inscribed with optimum parameters and etched is presented in FIG. 12. An AFM scan was performed on a 42.9 by 42.9 μm section and the RMS and peak-peak surface roughnesses were sampled over 100 μm² areas. Average roughness values of 91.5 nm and 323.6 nm were found for RMS and peak-peak respectively.

Figure 13:
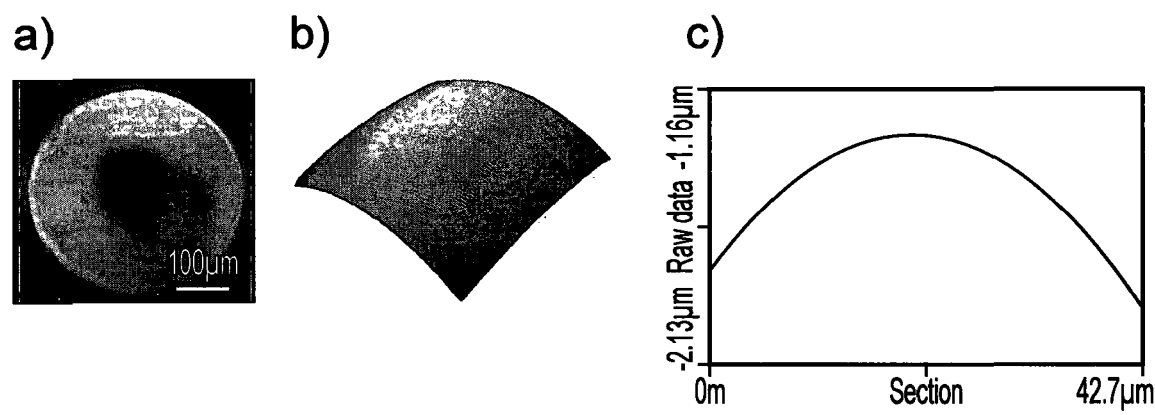
FIG. 13a is a micrograph of the fabricated microlens after undergoing flame polishing.
FIGS. 13b and 13c repeated AFM scan data of the polished lens showing the surface topography of a 42 µm square section and the corresponding line profile.

The same microlens was then flame polished as described above and measurements of the surface roughness repeated. The results of the AFM scan are presented in FIG. 13. It has been found that the surface quality to be significantly improved with the average RMS and peak to peak measured to be 2.15 nm and 6.16 nm and be respectively. These correspond to a reduction in the RMS surface roughness to 2.34% of the roughness of the unpolished lens.

The high spatial frequency roughness observed for the lens in FIG. 12 is now smoothed out over the surface and an RMS roughness of 2.15 nm was reported.

Surface Profile

Figure 14:
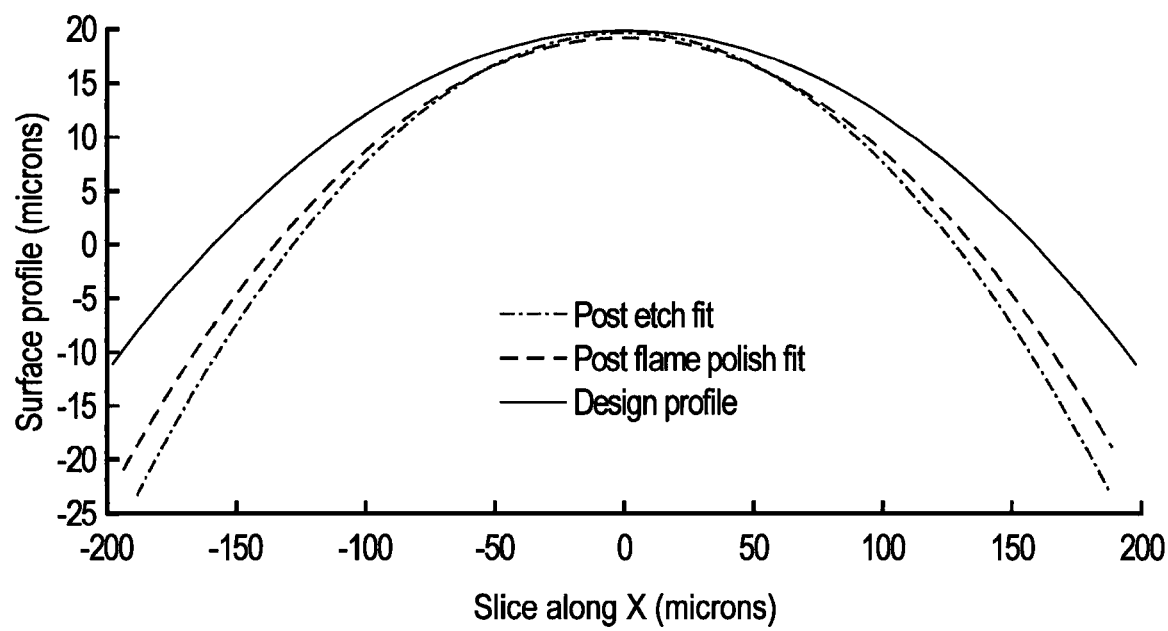
FIG. 14 is a plot of the measured lens profile before and after flame polishing with the inscribed profile for comparison. The polished lens has a slightly less steep, and therefore more spherical surface profile. The difference between the inscribed lens and the etched lens occurs due to etching of the pristine material in the areas surrounding the inscribed path.

In order to compare the form of the etched lens, both before and after flame polishing, with that inscribed, the surface was profiled using a white light interferometer. The measured data, along with a numerical fit, is plotted in FIG. 14.

There is a significant discrepancy between the etched lens and that inscribed. This can be explained by analysing etchant transport over the lens surface. The etchant penetrates from the edges of the surface, and so these regions experience a longer etching time than those near to the lens centre. In addition to this, areas of the lens with greater slope will etch more slowly due to the fixed orientation of nanogratings over the surface. The surface profile can be more closely replicated after etching by dynamically controlling the polarisation during inscription. The profile of the flame polished lens closely matches that of the unpolished lens. A decrease in the lens sag of ~1 μm was measured along with a noticeably shallower slope. While flame polishing, the liquid layer of glass flows to reduce surface area, taking approximately spherical form and flattening the slope. This unwanted effect can be compensated for during laser inscription.

Optical Throughput

Figure 15:
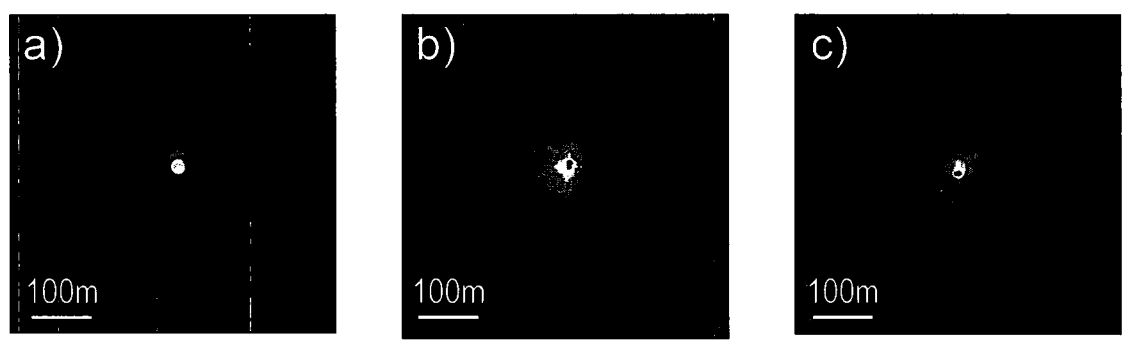
FIG. 15a is an image of the mode from the single mode fibre imaged onto a CCD and FIGS. 15b and 15c show the same fibre mode imaged through an inscribed microlens, both unpolished (b) and flame polished (c)

The power measured directly emerging from the fibre was 5.12±0.05 mW. The light detected after transmission through the lens both before and after flame polishing was 5.02±0.05 mW and 5.16±0.05 mW respectively. This corresponds to an optical throughput of 98.0±1.4% and 100.8±1.4% for the lens unpolished and flame polished respectively. The mode field launched from the fibre was imaged with the lens both before and after polishing and the spot diagrams are shown in FIG. 15.

Distal End Optical System (DOS)

FIGS. 16 through 21 show a distal end optical system (DOS) 100 for directing the light onto the target tissue and collecting the Raman signal. The DOS will depend greatly on a number of factors including the fibres chosen for light delivery and collection, the fibre configuration, and the actual application that the probe will be used for.

The specific values for the fibre geometries are an example and changes to these values are within the scope of the invention as described herein.

Figure 16:
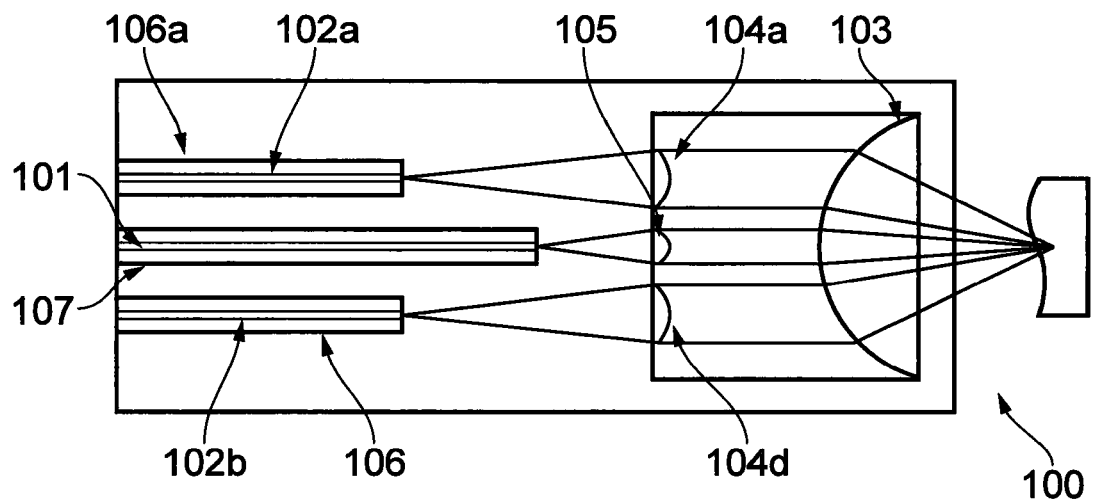
FIG. 16 shows a two-dimensional schematic of a distal end optical system (DOS) for delivering light through a central fibre and collecting back-scattered light using by six surrounding fibres.

The basic working principle of the device is shown schematically in FIG. 16. Pump light is delivered by single mode fibre 101 with a core diameter of 3.5 μm and cladding diameter 125 μm and a numerical aperture of 0.12. The fibre 101 will be coated with a narrow band filter to reject Raman forward scatter generated in the core and then inserted into the centre slot/channel 107 of the DOS. Six multimode collection fibres 102a, 102b with core and cladding diameters of 50 μm and 125 μm respectively and an NA of 0.22 are to be coated with a high pass filter to reject light at the pump wavelength from entering the fibre. These are inserted into the remaining six fibre slots/channels 106a to 106f. The pump light is collimated before being focused down onto a target behind the back of the DOS 101. The generated Raman signal emits in all directions. Some of that signal will radiate back into the DOS 101, collimate through the focusing lens 103 and couple into the collection fibres 102a, 102b through a collection lens ring array 104.

To optimise the device, ray tracing software 'Zemax' was used. Firstly, each lens was modelled individually in 'sequential' mode. In sequential mode, ray equations are solved from one surface to the next, for predefined specifications such as wavelength and NA. Zemax allows a 'merit function' to be defined, which is used to optimise an optical system based on the user's requirements. Such requirements are inputted to the merit function in the form of 'operands'.

Figure 17:
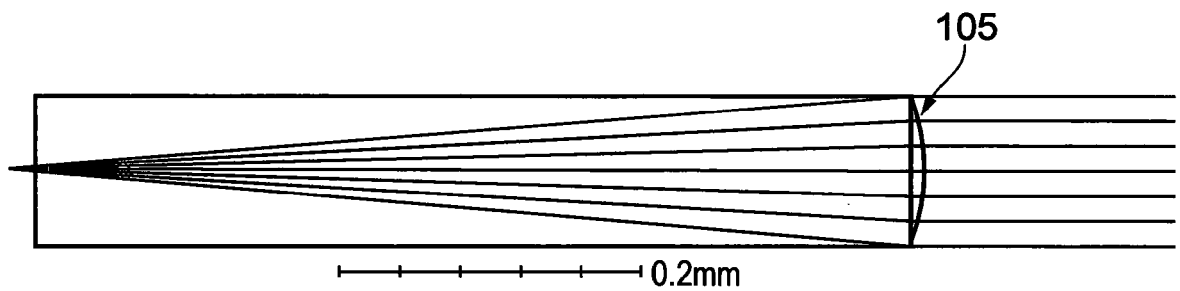
FIG. 17 shows the results of modelling of the lens that is used to collimate excitation light from the fibre after diverging through a length of the micro-optic.
Figure 18:
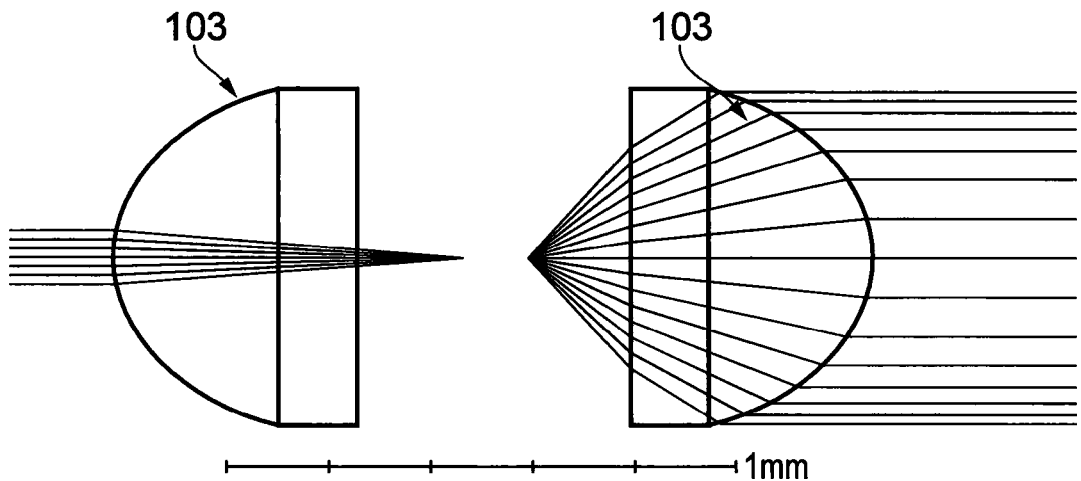
FIG. 18 shows the results of modelling of the focusing lens in the focusing configuration (left) and collimation configuration (right) that will focus down pump light onto the sample and collimate the returning Raman signal.
Figure 19:
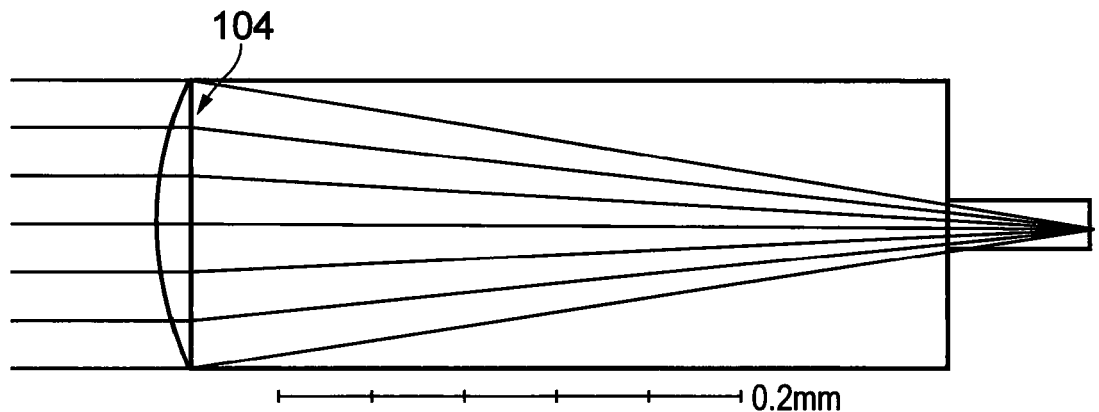
FIG. 19 shows the results of modelling a Raman signal coupling into a multimode fibre with 50 μm core diameter.

The fibres will be inserted and glued into slots etched out from the device. The glue is selected to index match the fibre core with the substrate in order to minimise refraction of light and scattering upon entering the device. The function of the first transmission lens 105 that the light encounters is to collimate the beam as shown in FIG. 17. The light leaves the 3.5 μm core of the single mode fibre at an NA of 0.12. In order to maximise the sensing efficiency, it is essential to fill the transmission lens aperture completely. To achieve this, an operand was added to the merit function that set the maximum ray height to the chosen semi-diameter, by varying the distance to the transmission lens 105. To optimise the transmission lens shape for collimation, an operand that solved for the ray angle of incidence at the image plane was used, with the target set to 0°. The function then solved for optimal radius and a conic constant of an aspheric surface to obtain the results shown.

The next surface that the pump beam encounters is the focusing lens 103. The purpose of the focussing lens 103 is to focus the pump light onto the tissue behind the optic and then to collimate the Raman signal in the reverse direction. The excitation wavelength is 785 nm and the fingerprint range of interest introduces a shift between 800 and 1800 $cm^{-1}$. This relates to a Raman signal wavelength range between 837 and 914 nm. To model the focussing lens, multiple wavelengths spanning this range were selected to be solved simultaneously. The focussing lens 105 was optimised in the Raman signal collimation configuration (FIG. 18) since this signal transmits through the entire cross-section of the focussing lens whereas the pump light transmits through the centre only. The distance between the back of the micro-optic and the focal point was set to 200 μm, relating to a tissue depth that has been shown to be rich in pre-cancer identifiers. The lens was optimised for collimation using the same operands as with the first lens. The thickness of the back wall and the diameter of the lens were chosen to maximise the cone angle of accepted light without the occurrence of TIR on the lens surface while maintaining structural integrity.

The final structure that the light encounters is the collection lens ring array 104. The collection lens array 104 is a set of six identical lenses 104a to 104f that will couple the light into the multimode collection fibres. A single lens was modelled during the optimisation process, shown in FIG. 19. For the collection lens, the numerical aperture is 0.22. The spacing between the lens and the fibre end was optimised for an incident ray height (at the fibre tip) equal to the fibre core semi-diameter (50 μm) while maintaining an NA of 0.22. The diameter of the lens was designed to fill the space between the edge of the centre lens and the outer edge of the device, so as to maximise the fill factor and thus collected Raman signal. In this configuration the individual lenses in the ring array overlap. This allows one to achieve a maximum fill factor and should pose no foreseeable fabrication problems using ULI.

Figure 20:
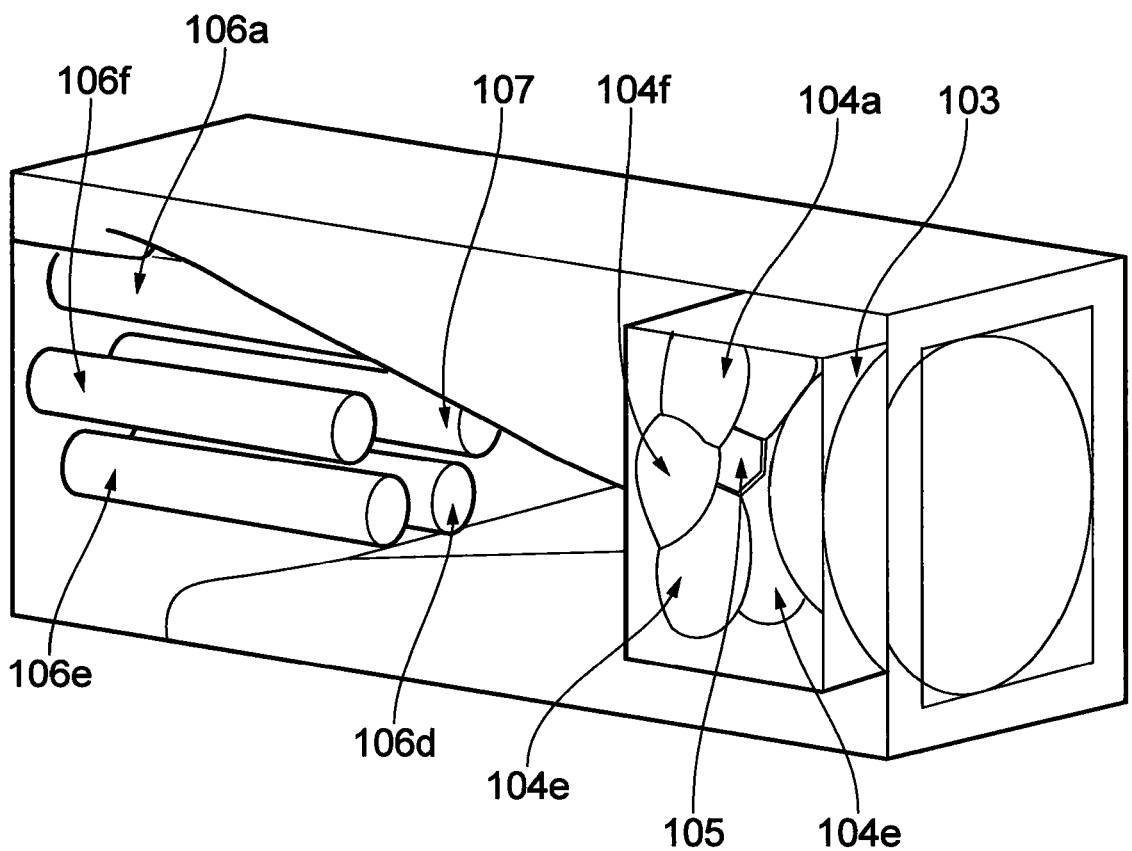
FIG. 20 shows a rendering of the assembled components that make up the DOS, wherein the Raman signal collection lenses overlap to maximise the signal detection efficiency.

The individual lens surfaces were assembled in a CAD modelling program; the complete device is shown in FIG. 20.

To model the device as a whole, sequential ray tracing proved insufficient because there are multiple sources of light (pump light and Raman signal) and the geometry is complex with many surfaces that stray light beams can interact with. Zemax also provides non-sequential ray tracing functionality, whereby the rays of light interact with surfaces in the physical order of which they meet, much like the real world. The non-sequential mode allows multiple sources, objects and detectors to be positioned freely in three-dimensional space, and so analysis of the pump light and the Raman signal detection can be performed simultaneously. It is important to note that when a CAD file is imported from an external source, geometry anomalies can be formed due to file type conversion, and these anomalies may influence the way individual light rays interact with the device during simulations.

Figure 21:
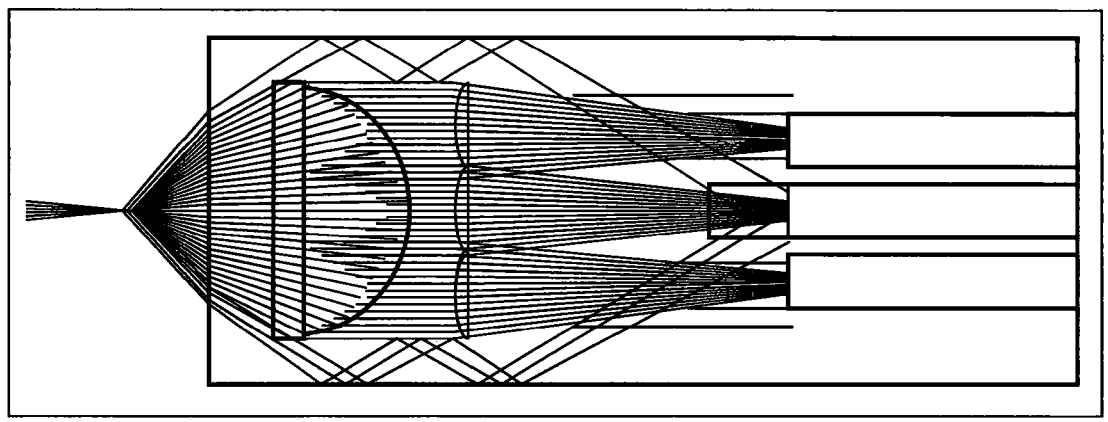

The excitation light is modelled as a point source with a cone angle related to an NA of 0.12 in fused silica, emerging from the end of the centre fibre slot. A second point source is placed to represent Raman scattering occurring at the pump light focal point. In practice, the Raman signal will be emitted equally in all directions, however, for modelling, a cone angle is selected which overfills the aperture of the focusing lens, so as to simulate reality more closely. FIG. 21 shows the paths taken by rays both entering and missing the aperture of the lens. A small fraction of rays is totally internally reflected along the sides of the DOS before being sent towards the collection fibres. It is not possible for this light to enter the fibres however as the angle of incidence exceeds that allowed by the NA. Any Raman signal that reaches the centre fibre will be rejected by the narrow band fibre coating.

Figure 22:
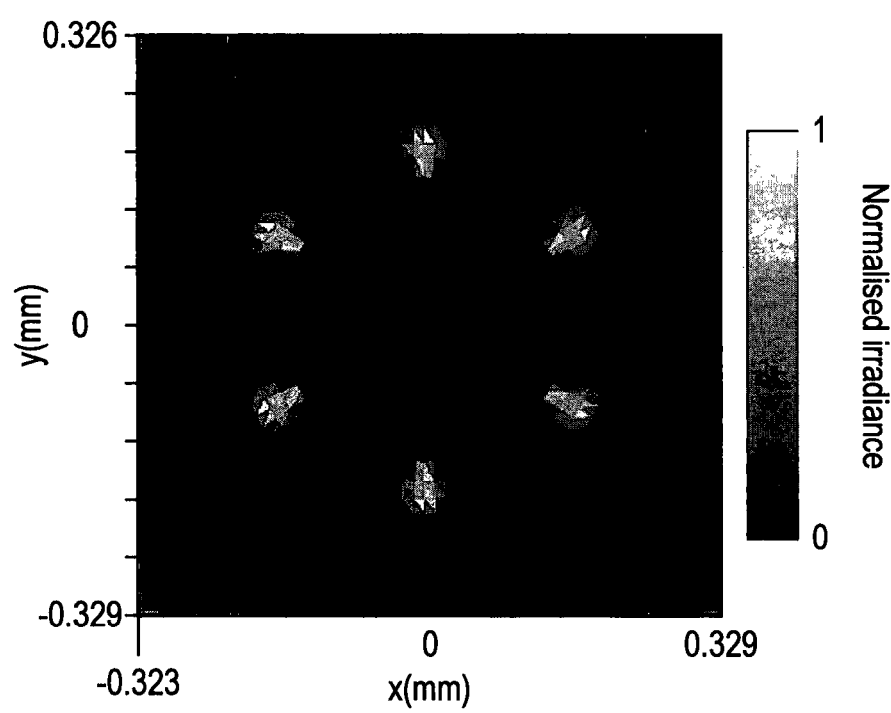
FIG. 22 is an intensity distribution of light incident on a detector plane situated at the entrance of the collection fibres.

The intensity distribution of light incident on the detection plane for a simulation for 500,000 rays is plotted in FIG. 22. There are clear intensity peaks marking the entrances to the collection fibre cores, each with diameters in the region of 50 μm relating to the core diameter. Since the lens system is symmetric around a central axis, one would expect each intensity peak to be symmetric about its own centre. This is not the case, however, and it is likely that the slight asymmetric shape is an artefact of the imported CAD file and not inherent to the system itself.

With ULI the ability to fabricate custom surfaces and lens profiles that give greater control over how the light is delivered and distributed into the target tissue.

Figure 23:
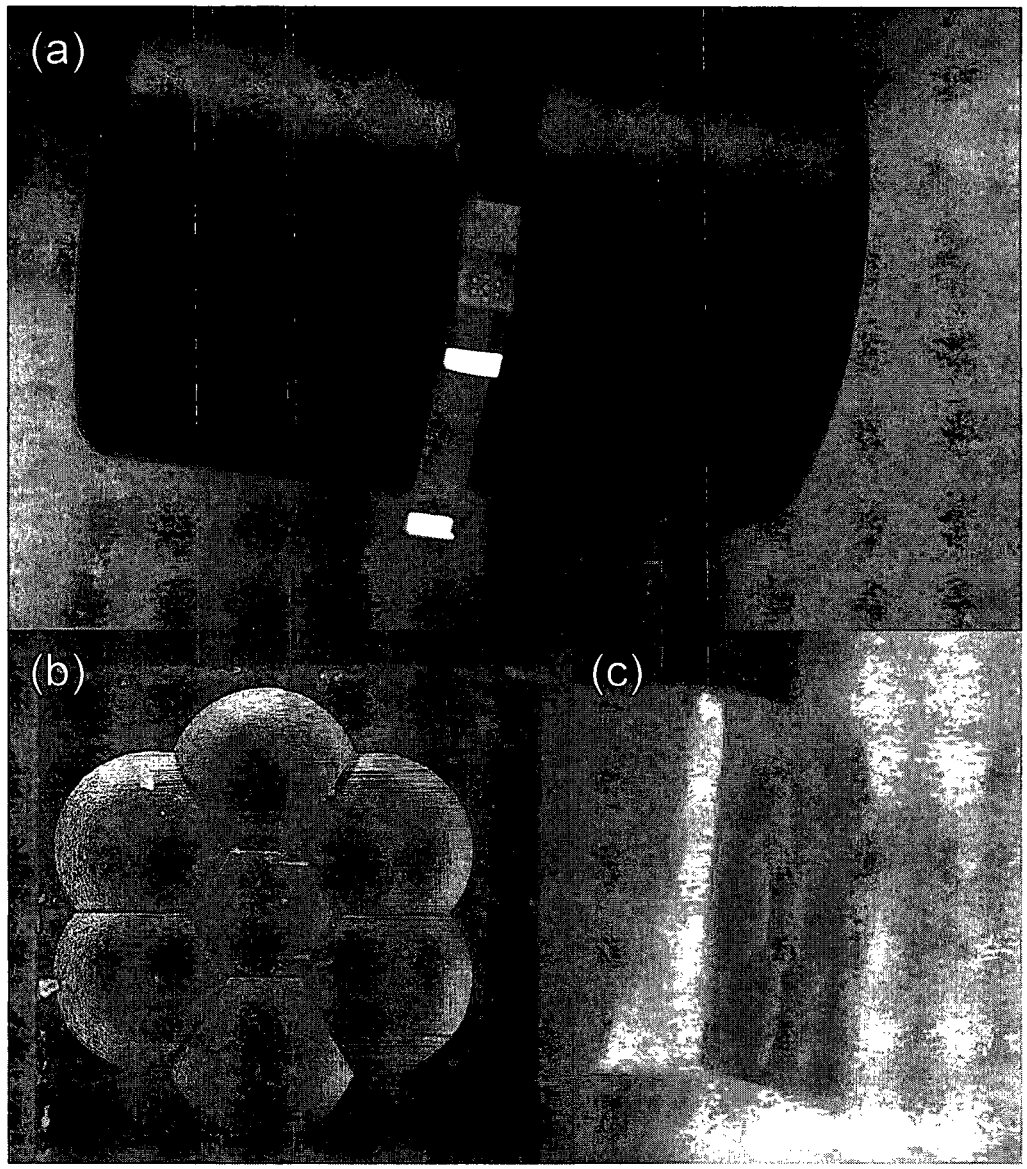
FIG. 23a is a photograph of the six around one micro-lens, FIG. 23b an optical micrographs of the micro-lens viewed from above and FIG. 23c an optical micrographs of the micro-lens at an angle.

An example of the around one "petal" lens arrangement, similar to that to be used in the DOS device was fabricated. The lens was fabricated at a 500 kHz repetition rate on the edge of a fused silica substrate, the thickness of which was designed to match the lens focal length FIG. 23a. Visually the surfaces of the micro-lens were observed to have some minor roughness, however no obvious artefacts were observed FIG. 23b.)

(c)

Figure 24:
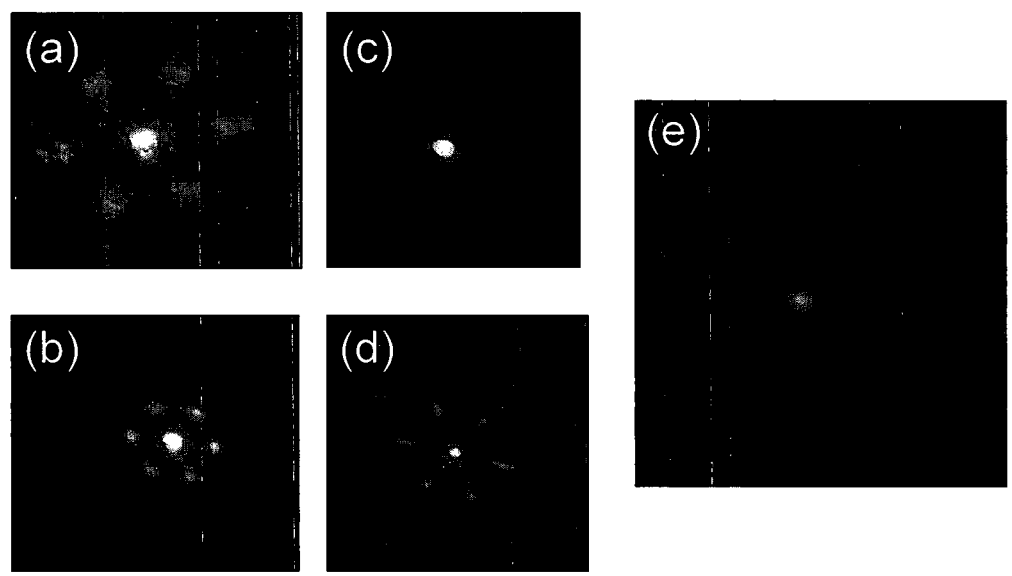
FIG. 24a is an image of 780 nm light through micro-lens array showing 7 diverging spots.
FIGS. 24b through 24d are images showing spots generated by 25 mm lens used to collect the light as they pass through the focus and FIG. 24e is a camera image of the 7 spots brought to a focus.

The petal micro-lens arrangement was again tested with a single mode fibre. With the fibre positioned slightly back from the sample to ensure the beam fully fills the micro-lens array a pattern of 7 spots that diverged relatively quickly was observed (FIG. 24a). A 25 mm focal length lens was used to focus the beams (FIG. 24b-d), and a very well defined focus, with minimal scattered light observed (FIG. 24e). At the focus, a power of 4.16 mW was measured compared to 4.6 mW with the micro-lens removed from the system. This demonstrates a high throughput. The majority of losses, in this case, are due to Fresnel losses at the fibre and the back of the micro-lens array, which will not be present in the completed device. e)

Figure 26:
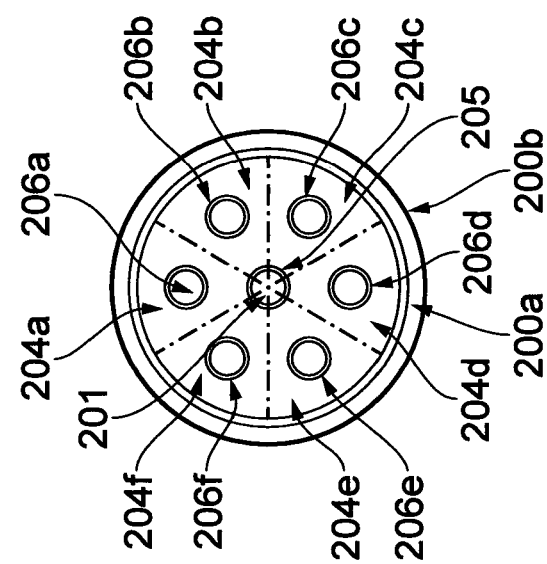
FIG. 26 is an end view of the distal-end optical system shown in FIG. 25.
Figure 25:
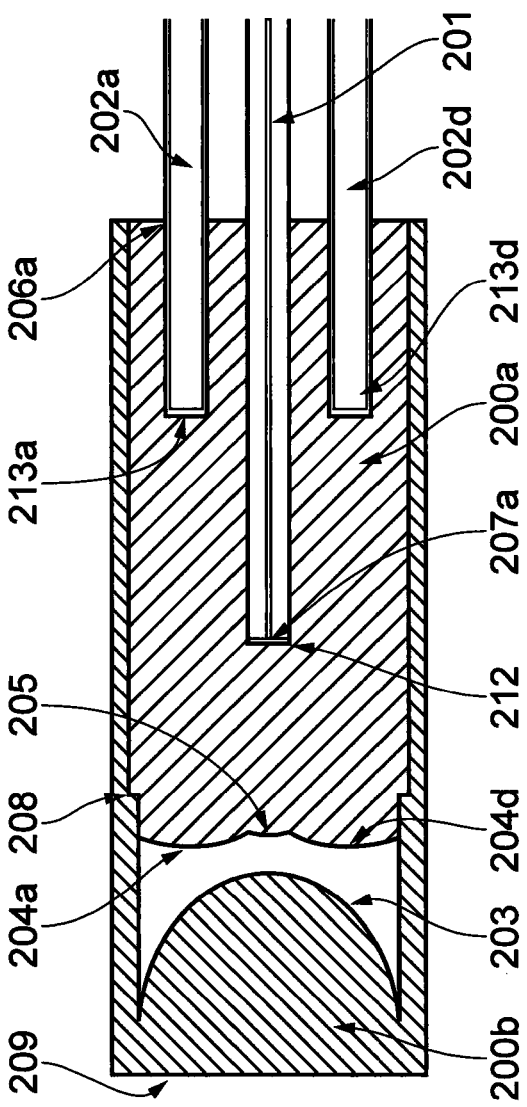
FIG. 25 is a sectional view of a distal-end optical system according to another embodiment of the invention.

A further embodiment of a distal-end optical system according to the invention is shown in FIGS. 25 and 26. In FIGS. 25 and 26, like reference numerals but in the series 200 have been used to refer to features of this embodiment that correspond to features of the previous embodiment described with reference to FIGS. 16 to 24. Reference is made to the description above for aspects of these features that are the same or similar to the previous embodiment.

A difference between this embodiment and the previous embodiment is that the distal-end system 200 is formed of two separate substrates/components 200a and 200b. A first component 200a comprises a unitary silica substrate having formed therein the collection lenses 204a to 204f, the first transmission lens/collimating lens 205 and the channels 206a to 206f and 207. A second component 200b comprises a unitary silica substrate having formed therein the focussing lens 203. The first component 200a forms a male connecting member for insertion into an aperture of the second component 200b. In this respect, the second component 200b comprises a hollow receiving section 208 capped by the focussing lens 203, the hollow receiving section 208 dimensioned for receiving the first component 200a. The receiving section 208 has a stepped internal profile 208, wherein the step is arranged to engage with a corresponding step in an outer profile of the first component 200a to limit the extent that the first component 200a can be inserted into the component 200b.

Providing the optical surfaces 204a to 204f, 205 and 203 inside a cavity formed by the assembled components 200a and 200b ensures that contact of the distal-end system with patient tissues does not impact the performance of these optical surfaces. A back surface 209 of the focussing lens 203, which does contact patient tissues, is optically polished.

The petal design of the collection and collimating lenses 204a to 204f and 205 differs from the other embodiment in that the collimating lens 205 has a circular rather than hexagonal aperture, as can be seen in FIG. 26, and each collection lens 204a to 204f has an aperture having an inner curved border corresponding to the outer extent of the collimating lens 205. In this embodiment, the collimating lens has a diameter of 100 μm and the outer diameter of the collecting lenses 204a to 204f is 800 μm.

Both the focussing lens 203 and the collection lenses 204a to 204f have aspherical surface profiles.

The light delivery fibre 201 has a small NA so that the light emerging from it has a low divergence and fully fills the central collimating lens 205. The channel 207 and, therefore the central fibre 201, is also terminated 207a nearer to a surface of lens 205 so that the excitation light has a small footprint on the petal surface. A distal end of the delivery optical fibre 201 is coated 212 to filter out unwanted wavelengths of light, such as Raman background, generated in the delivery fibre 201.

Figure 27:
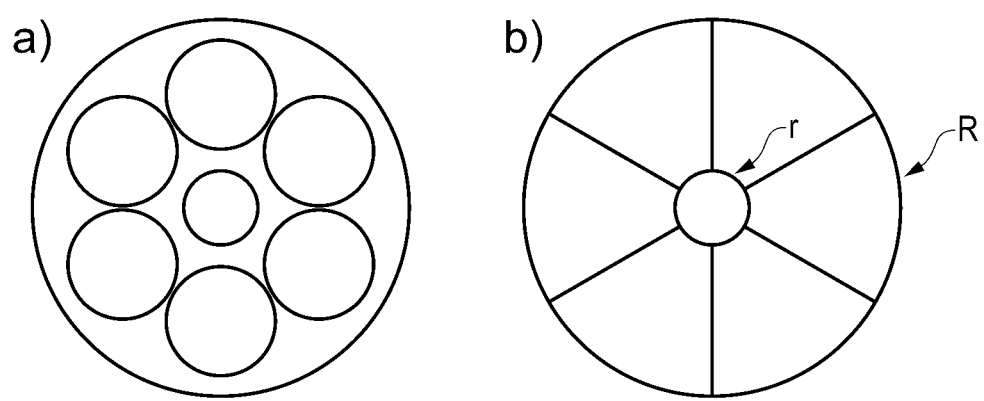
FIGS. 27a and 27b show two lens surfaces a) with an array of circular collection lens and b) an array of collection lenses having an overlapping "petal" design.

The fill factor, FF, of the lens petal surface is defined as the fraction of the surface which will collect light that falls upon it. This is given by one minus the ratio of the areas of the circles defined by r and R in FIG. 27b.

$$FF = \frac{(R^2 - r^2)}{R^2}$$

The amount of light collected, I, is proportional to the surface area of the petal lens. The distal-end optical device 200 described is calculated as having a FF of 0.984 or a theoretical collection efficiency of 98.4%. This is much higher than for a surface in which the six lenses have a circular aperture as shown in FIG. 2.

The ends of the collection optical fibres 202a to 202f are coated 213a, 213d to filter unwanted fluorescence and the backscattered excitation light.

The fibre optics are coupled to the distal-end system by gluing the fibre optics in the corresponding channel 206a to 206f, 207. Insertion of the fibre optics into the channels acts to align the end of the fibre optics with the corresponding lens. The collection fibres 202a to 202f are large core multimode optical fibres relative to the small core single-mode optical fibre 207 used for the delivery fibre. The large numerical aperture of the collection fibres 202a to 202f aids fibre coupling and light collection whereas the small numerical aperture of the delivery fibre keeps the footprint of the excitation light on the lens surface relatively small.

CONCLUSIONS

The contribution of various inscription parameters on the etch-rate of fused silica in order to optimise the ULI and chemical etching fabrication process of 3D microstructures has been explained. The formation and arrangement of 'nanogratings' plays a role in allowing the etchant to penetrate quickly through the glass. By inscribing a surface with the laser polarisation set perpendicular to it, nanoplanes formed parallel with the surface and enhanced etching. By doing so etch-rate selectivities of up to 100 for pulse energies between 150 and 200 nJ were obtained, optimal for Type II modification. Along with enhancing the etch-rate, nanogratings formed permanent features on inscribed surfaces after etching. Surface roughness can be decreased by approximately five-fold by precisely controlling the polarisation during inscription. 3D structures are typically inscribed layer by layer, analogous to 3D printing. The spacing between layers could be increased from 1 μm to 10 μm with little or no reduction in the etch-rate, but with increased surface roughness. With this knowledge, the inscription time can be reduced significantly for structures with no optical requirement. The ability to fabricate a microlens, with a surface roughness corresponding to $\sim\lambda/10$ for visible to NIR wavelengths, with a throughput of 98.0% at 780 nm has been demonstrated. With flame polishing, a surface roughness has been decreased down to approximately $\lambda/360$ and increased the throughput to 100% within experimental error, while maintaining the overall lens profile. An unpolished lens would be suitable for optical applications involving the guiding and collection of light, whereas the polished lens should be suitable for micro-imaging, even at shorter wavelengths.

(d)

REFERENCES

[1] Davis, K. M., Miura, K., Sugimoto, N. et al., "Writing waveguides in glass with a femtosecond laser," Optics Letters, 21(21), 1729-1731 (1996).
[2] Thomson, R. R., Harris, R. J., Birks, T. A. et al., "Ultrafast laser inscription of a 121-waveguide fan-out for astrophotonics," Optics Letters, 37(12), 2331-2333 (2012).
[3] Chen, F., and de Aldana, J. R. V., "Optical waveguides in crystalline dielectric materials produced by femtosecond-laser micromachining," Laser & Photonics Reviews, 8(2), 251-275 (2014).
[4] Marshall, G. D., Ams, M., and Withford, M. J., "Direct laser written waveguide-Bragg gratings in bulk fused silica," Optics Letters, 31(18), 2690-2691 (2006).
[5] Nolte, S., Will, M., Burghoff, J. et al., "Femtosecond waveguide writing: a new avenue to three-dimensional integrated optics," Applied Physics a-Materials Science & Processing, 77(1), 109-111 (2003).
[6] Hirao, K., and Miura, K., "Writing waveguides and gratings in silica and related materials by a femtosecond laser," Journal of Non-Crystalline Solids, 239(1-3), 91-95 (1998).
[7] Choudhury, D., Arriola, A., Allington-Smith, J. R. et al., "Towards freeform microlens arrays for near infrared astronomical instruments," Proceedings of SPIE. 9151 (2014).
[8] Wu, D., Xu, J., Niu, L. G. et al., "In-channel integration of designable microoptical devices using flat scaffold-supported femtosecond-laser microfabrication for coupling-free optofluidic cell counting," Light-Science & Applications, 4, 8 (2015).
[9] Sugioka, K., and Cheng, Y., "Fabrication of 3D microfluidic structures inside glass by femtosecond laser micromachining," Applied Physics a-Materials Science & Processing, 114(1), 215-221 (2014).
[10] Horstmann-Jungemann, M., Gottmann, J., and Wortmann, D., "Nano- and Microstructuring of SiO2 and Sapphire with Fs-laser Induced Selective Etching," Journal of Laser Micro Nanoengineering, 4(2), 135-140 (2009).
[11] Bhardwaj, V. R., Simova, E., Rajeev, P. P. et al., "Optically produced arrays of planar nanostructures inside fused silica," Physical Review Letters, 96(5), 4 (2006).
[12] He, F., Cheng, Y., Qiao, L. L. et al., "Two-photon fluorescence excitation with a microlens fabricated on the fused silica chip by femtosecond laser micromachining," Applied Physics Letters, 96(4), (2010).
[13] Bellouard, Y., Barthel, E., Said, A. A. et al., "Scanning thermal microscopy and Raman analysis of bulk fused silica exposed to low-energy femtosecond laser pulses," Optics Express, 16(24), 19520-19534 (2008).
[14] Hnatovsky, C., Taylor, R. S., Rajeev, P. P. et al., "Pulse duration dependence of femtosecond-laser-fabricated nanogratings in fused silica," Applied Physics Letters, 87(1), (2005).
[15] Shimotsuma, Y., Kazansky, P. G., Qiu, J. R. et al., "Self-organized nanogratings in glass irradiated by ultrashort light pulses," Physical Review Letters, 91(24), 4 (2003).
[16] Glezer, E. N., and Mazur, E., "Ultrafast-laser driven micro-explosions in transparent materials," Applied Physics Letters, 71(7), 882-884 (1997).
[17] Liao, Y., Pan, W. J., Cui, Y. et al., "Formation of in-volume nanogratings with sub-100-nm periods in glass by femtosecond laser irradiation," Optics Letters, 40(15), 3623-3626 (2015).
[18] Kang, J. K., and Musgrave, C. B., "The mechanism of HF/H2O chemical etching of SiO2," Journal of Chemical Physics, 116(1), 275-280 (2002).
[19] Marcinkevicius, A., Juodkazis, S., Watanabe, M. et al., "Femtosecond laser-assisted three-dimensional microfabrication in silica," Optics Letters, 26(5), 277-279 (2001).
[20] Hnatovsky, C., Taylor, R. S., Simova, E. et al., "Polarization-selective etching in femtosecond laser-assisted microfluidic channel fabrication in fused silica," Optics Letters, 30(14), 1867-1869 (2005).
[21] Bellouard, Y., Said, A., Dugan, M. et al., "Fabrication of high-aspect ratio, micro-fluidic channels and tunnels using femtosecond laser pulses and chemical etching," Optics Express, 12(10), 2120-2129 (2004).
[22] Agarwal, A., and Tomozawa, M., "Correlation of silica glass properties with the infrared spectra," Journal of Non-Crystalline Solids, 209(1-2), 166-174 (1997).

[23] Taylor, R., Hnatovsky, C., and Simova, E., "Applications of femtosecond laser induced self-organized planar nanocracks inside fused silica glass," Laser & Photonics Reviews, 2(1-2), 26-46 (2008).

[24] Canning, J., Lancry, M., Cook, K. et al., "Anatomy of a femtosecond laser processed silica waveguide Invited," Optical Materials Express, 1(5), 998-1008 (2011).

[25] Fiorin, R., da Costa, L. N., Abe, I. et al., "Manufacturing of microchannels in soda-lime glass by femtosecond laser and chemical etching," 2013 Sbmo/Ieee Mtt-S International Microwave & Optoelectronics Conference (Imoc), 3 (2013).

[26] Richter, S., Heinrich, M., Doring, S. et al., "Formation of femtosecond laser-induced nanogratings at high repetition rates," Applied Physics a-Materials Science & Processing, 104(2), 503-507 (2011).

[27] Drs, J., Kishi, T., and Bellouard, Y., "Laser-assisted morphing of complex three dimensional objects," Optics Express, 23(13), 17355-17366 (2015).

The invention claimed is:

1. An optical device comprising:
a unitary substrate of optically transparent material, the unitary substrate having formed therein at least one collection lens and at least one collection channel, each collection channel of the at least one collection channel (i) being for receiving a corresponding collection optical fibre and (ii) being arranged to align the corresponding collection optical fibre inserted therein such that a corresponding lens of the at least one collection lens couples light collected by the corresponding collection lens into the corresponding collection optical fibre; and
a focusing lens for focusing excitation light to a focal point outside of the unitary substrate,
wherein each lens of the at least one collection lens is configured to couple light scattered from an object at the focal point into the corresponding collection optical fibre.

2. The optical device according to claim 1, wherein each lens of the at least one collection lens is arranged to focus the collected light to a point at an end of or within the corresponding collection optical fibre.

3. The optical device according to claim 1, wherein the unitary substrate has formed therein a transmission lens and a delivery channel for receiving a delivery optical fibre, the delivery channel being arranged to align the delivery optical fibre inserted therein such that excitation light delivered by the delivery optical fibre impinges on the transmission lens.

4. The optical device according to claim 3, wherein the transmission lens is a collimating lens for collimating the excitation light.

5. The optical device according to claim 3, wherein the delivery channel terminates closer to the transmission lens than where each channel of the at least one collection channel terminates relative to the corresponding collection lens.

6. The optical device according to claim 1, wherein the at least one collection lens comprises a plurality of collection lenses and the at least one collection channel comprises a plurality of collection channels, each lens of the collection lenses having a corresponding one of the plurality of collection channels associated therewith.

7. The optical device according to claim 6, wherein the plurality of collection lenses are arranged in a petal design.

8. The optical device according to claim 7, wherein the petal design comprises the plurality of collection lenses providing a continuum of collection lenses in a circle or annulus.

9. The optical device according to claim 7,
wherein the unitary substrate has formed therein a transmission lens and a delivery channel for receiving a delivery optical fibre, the delivery channel being arranged to align the delivery optical fibre inserted therein such that excitation light delivered by the delivery optical fibre impinges on the transmission lens, and
wherein the petal design of collection lenses is centred around the transmission lens.

10. The optical device according to claim 9, wherein the plurality of collection lenses is arranged in an annulus surrounding the transmission lens.

11. The optical device according to claim 10, wherein each of the plurality of collection lenses extends out from the transmission lens.

12. The optical device according to claim 6, wherein an aperture of each lens of the plurality of collection lenses is non-circular.

13. The optical device according to claim 12, wherein the aperture of each lens of the plurality of collection lenses is a circular or annulus sector.

14. The optical device according to claim 1,
wherein the focusing lens is for collimating light originating from the focal point exposed to the excitation light and directing the collimated light onto the at least one collection lens, and
wherein a fraction of an aperture of the collimated light filled by the at least one collection lens is greater than $2/3$.

15. The optical device according to claim 1, wherein the optical device is an endoscope.

16. The optical device according to claim 15, wherein the unitary substrate forms part of a distal end of the endoscope.

17. The optical device according to claim 15, further comprising at least one of the collection optical fibres, each collection channel of the unitary substrate having a corresponding one of the collection optical fibres therein.

18. The optical device according to claim 15,
wherein the unitary substrate has formed therein a transmission lens and a delivery channel for receiving a delivery optical fibre, the delivery channel arranged to align the delivery optical fibre inserted therein such that excitation light delivered by the delivery optical fibre impinges on the transmission lens, and
wherein the optical device further comprises the delivery optical fibre, the delivery optical fibre being received in the delivery channel of the unitary substrate.

19. A method of forming an optical device according to claim 1, the method comprising forming a laser inscribed substrate by selectively laser inscribing an optically transparent substrate and chemically etching the laser inscribed substrate to remove material of the laser inscribed substrate.

20. The optical device according to claim 1, wherein each lens of the at least one collection lens is configured to couple light back-scattered from the focal point into the corresponding collection optical fibre.

21. The optical device according to claim 1, wherein each lens of the at least one collection lens is configured to couple light that is Raman-scattered from the focal point into the corresponding collection optical fibre.

22. An optical device comprising:
a unitary substrate of optically transparent material, the unitary substrate having formed therein at least one collection lens and at least one collection channel, each collection channel being for receiving a corresponding collection optical fibre, and each collection channel being arranged to align the corresponding collection optical fibre inserted therein such that a corresponding lens of the at least one collection lens couples light collected by the corresponding collection lens into the corresponding collection optical fibre; and a further, separate substrate comprising a focusing lens for focusing excitation light to a point and for collimating light originating from the focal point exposed to excitation light, the further, separate substrate being connected to the unitary substrate by a connecting formation.

* * * * *